(12) United States Patent
Rahbar

(10) Patent No.: US 6,787,566 B2
(45) Date of Patent: Sep. 7, 2004

(54) BREAKERS OF ADVANCED GLYCATION ENDPRODUCTS

(75) Inventor: Samuel Rahbar, Encino, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/825,925

(22) Filed: Apr. 5, 2001

(65) Prior Publication Data

US 2002/0002203 A1 Jan. 3, 2002

Related U.S. Application Data

(63) Continuation-in-part of application No. 09/800,976, filed on Mar. 8, 2001, which is a continuation-in-part of application No. 09/543,703, filed on Apr. 5, 2000, and a continuation-in-part of application No. 09/626,859, filed on Jul. 27, 2000, which is a continuation-in-part of application No. 09/543,703, filed on Apr. 5, 2000, and a continuation-in-part of application No. 09/559,913, filed on Apr. 28, 2000.
(60) Provisional application No. 60/127,835, filed on Apr. 5, 1999, and provisional application No. 60/131,675, filed on Apr. 29, 1999.

(51) Int. Cl.$^7$ ................... A61K 31/195; A61K 31/192; A61P 31/10
(52) U.S. Cl. ........................ 514/563; 514/571; 562/439
(58) Field of Search ............................... 514/571, 563, 514/596, 634, 564, 567, 330

(56) References Cited

U.S. PATENT DOCUMENTS

| 5,272,176 A | 12/1993 | Ulrich et al. ............... 514/399 |
| 5,661,139 A | 8/1997 | Lankin et al. ................ 560/34 |

FOREIGN PATENT DOCUMENTS

| WO | WO 92/07560 A1 | 5/1992 |
| WO | WO 95/31192 | 11/1995 |
| WO | WO 00/59875 A2 | 10/2000 |

OTHER PUBLICATIONS

Al–Abed, Y. et al. "Inhibition of advanced glycation endproduct formation by acetaldehyde: Role in the cardioprotective effect of ethanol", *Proc. Natl. Acad. Sci. USA*, Mar. 1999; 96:2385–2390.

Asif, M. et al. "An advanced glycation endproduct cross–link breaker can reverse age–related increases in myocardial stiffness", *PNAS*, Mar. 14, 2000; 97(6):2809–2813.

Boel, E. et al. "Diabetic Late Complications: Will Aldose Reductase Inhibitors or Inhibitors of Advanced Glycosylation Endproduct Formation Hold Promise?", *J. Diabetes and its Complications*, 1995; 9:104–129.

Booth, A.A. et al. "Thiamine Pyrophosphate and Pyridoxamine Inhibit the Formation of Antigenic Advanced Glycation End–Products: Comparison with Aminoguanidine", *Biochem. Biophys. Res. Commun.*, 1996; 220:113–119.

Booth, A.A. et al. "In Vitro Kinetic Studies of Formation of Antigenic Advanced Glycation End Products (AGEs)", *Journal of Biological Chemistry*, Feb. 28, 1997; 272(9):5430–5437.

Calatayud J.J., "Favorable Effects of the Lipid–Lowering and Platelet Antiaggregant Plafibride on the Aging Process of Mice of the C57BL/6J Strain," *Math and Find Exptl Clin Pharmacol*, 1983; 5(10):707–714.

Cameron, N.E. et al. "Effects of aminoguanidine on peripheral nerve function and polyol pathway metabolites in Streptozotocin–diabetic rats", *Diabetologia*; 1992; 35:946–950.

Corbett, J.A. et al. "Aminoguanidine, a Novel Inhibitor of Nitric Oxide Formation, Prevents Diabetic Vascular Dysfunction", *Diabetes*, Apr. 1992; 41:552–556.

Cooper, M.E. et al., "The cross–link breaker, N–phenacylthiazolium bromide prevents vascular advanced glycation end–product accumulation," *Diabetologia*, 2000; 43:660–664.

Durany, N. et al. "Investigations on oxidative stress and therapeutical implications in dementia", *Eur. Arch. Psychiatry Clin. Neurosci.*, 1999; 249:Suppl. 3 III/68–III/73.

Hirsch, J. et al., "The reaction of some dicarbonyl sugars with aminoguanidine," *Carbohydrate Research*, 1992; 232:125–130.

Jakus, V. et al. "Inhibition of Nonenzymatic Protein Glycation and Lipid Peroxidation by Drugs with Antioxidant Activity", *Life Sciences*, 1999; 65(18–19):1991–1993.

Jyothirmayi, G.N. et al. "Effects of Metformin on Collagen Glycation and Diastolic Dysfunction in Diabetic Myocardium", *J. Cardiovasc. Pharmacol. Therapeut.*, 1998; 3(4):319–326.

Khalifah, R.G. "Amadorins: Novel Post–Amadori Inhibitors of Advanced Glycation Reactions", *Biochem. Biophys. Res. Commun.*, 1999; 257–258.

(List continued on next page.)

Primary Examiner—Richard L. Raymon
Assistant Examiner—Venkataraman Balasubramanian
(74) Attorney, Agent, or Firm—Rothwell, Figg, Ernst & Manbeck, P.C.

(57) ABSTRACT

Advanced glycation endproducts (AGEs) have been implicated in the pathogenesis of a variety of debilitating diseases such as diabetes, atherosclerosis, Alzheimer's and rheumatoid arthritis, as well as in the normal aging process. Seven compounds are here reported to be active in breaking AGE-protein cross-links. These compounds are 1,4-benzene-bis[4-methyleneaminophenoxyisobutyric acid] (LR102); 4-[(3,5-dichlorophenylureidophenoxyisobutyryl]-4-aminobenzoic acid (LR99); L-bis-[4-(4-chlorobenzamidophenoxyisobutyryl)cystine] (LR20); 4-(3, 5-dichlorophenylureido)phenoxyisobutyryl-1-amidocyclohexane-1-carboxylic acid (LR23); methylene bis [4,4'-(2-chlorophenylureidophenoxyisobutyric acid)] (LR90); 5-aminosalicylic acid (5-ASA); and metformin. These compounds may be used to reverse the debilitating effects of those diseases in which AGEs are formed.

12 Claims, 9 Drawing Sheets

OTHER PUBLICATIONS

Kochakian, M. et al. "Chronic Dosing with Aminoguanidine and Novel Advanced Glycosylation End Product–Formation Inhibitors Ameliorates Cross–Linking of Tail Tendon Collagen and STZ–Induced Diabetic Rats", *Diabetes*, Dec. 1996; 45:1694–1700.

Malik, N.S. and Meek, K.M. "The Inhibition of Sugar–Induced Structural Alterations in Collagen by Aspirin and Other Compounds", *Biochem. Biophys. Res. Commun.*, 1994; 199(2):683–686.

Marques, C. et al. "Bendazac decreases in vitro glycation of human lens crystallins. Decrease of in vitro protein glycation by bendazac", *Documenta Ophthalmologica*, 1995; 90:395–404.

Menzel, E.J. et al. "Comparison of the effect of different inhibitors on the non–enzymatic glycation of rat tail tendons and bovine serum albumin", *Ann. Clin. Biochem.*, 1996; 33:241–248.

Miwa, I. et al. "Inhibition of Advanced Protein Glycation by 8–Quinolinecarboxylic Hydrazide", *Pharmacology*, 1996; 52:314–320.

Morimitsu, Y. et al. "Protein Glycation Inhibitors from Thyme (*Thymus vulgaris*)", *Biosci. Biotech. Biochem.*, 1995; 59(11):2018–2021.

Münch, G. et al. "Influence of advanced glycation end–products and AGE–inhibitors on Nucleation–dependent polymerization of β–amyloid peptide", *Biochimica et Biophysica Acta*, 1997; 1360:17–29.

Münch, G. et al. "Advanced glycation endproducts in ageing and Alzheimer's disease", *Brain Research Reviews*, 1997; 23:134–143.

Nakamura, S. et al. "Progression of Nephropathy in Spontaneous Diabetic Rats is Prevented by OPB–9195, a Novel Inhibitor of Advanced Glycation", *Diabetes*, May 1997; 46:895–899.

Rahbar, S. and Nadler, J.L. "A new rapid method to detect inhibition of Amadori product generated by $\delta$–gluconolactone", *Clinica Chimica Acta*, 1999; 287:123–130.

Rahbar, S. et al. "Novel Inhibitors of Advanced Glycation Endproducts", *Biochem. Biophys. Res. Commun.*, 1999; 262:651–656.

Raj D.S.C., et al., "Advanced Glycation End Products: A Nephrologist's Perspective," American Journal of Kidney Diseases, Mar. 2000; 35(3):365–380.

Ruggiero–Lopez, D. et al. "Reaction of Metformin with Dicarbonyl Compounds. Possible Implication in the Inhibition of Advanced Glycation End Product Formation", *Biochem. Pharmacology*, 1999; 58:1765–1773.

Ryan, M.E. et al. "Tetracyclines Inhibit Protein Glycation in Experimental Diabetes", *Adv. Dent. Res.*, Nov. 1998; 12:152–158.

Sensi, M. et al. "D–Lysine reduces the non–enzymatic glycation of proteins in experimental diabetes mellitus in rats", *Diabetologia*, 1993; 36:797–801.

Soulis, T. et al. "Relative contributions of advanced glycation and nitric oxide synthase inhibition to aminoguanidine-mediated renoprotection in diabetic rats", *Diabetologia*, 1997; 40:1141–1151.

Soulis, T. et al. "A novel inhibitor of advanced glycation end–product formation inhibits mesenteric vascular hypertrophy in experimental diabetes", *Diabetologia* 1999; 42:472–479.

Swamy–Mruthinti, S. et al. "Acetyl–L–Carnitine Decreases Glycation of Lens Proteins: in vitro Studies", *Exp. Eye Res.*, 1999; 69:109–115.

Taguchi, T. et al. "Inhibition of advanced protein glycation by a Schiff base between aminoguanidine and pyridoxal", *European Journal of Pharmacology*, 1999; 378:283–289.

Tanaka, Y. et al. "Effect of metformin on advanced glycation endproduct formation and peripheral nerve function in streptozotocin–induced diabetic rats", *European Journal of Pharmacology*, 1999; 376:17–22.

Thornally, P.J. et al., "Rapid Hydrolysis and Slow α, β–Dicarbonyl Cleavage of an Agent Proposed to Cleave Glucose–Derived Protein Cross–Links," Biochemical Pharmacology, 1999; 57:303–307.

Tilton, R.G. et al. "Prevention of Diabetic Vascular Dysfunction by Guanidines. Inhibition of Nitric Oxide Synthase Versus Advanced Glycation End–Product Formation", *Diabetes*, Feb. 1993; 42:221–232.

Tsuchida, K. et al. "Suppression of transforming growth factor beta and vascular endothelial growth factor in diabetic nephropathy in rats by a novel advanced glycation end product inhibitor, OPB–9195", *Diabetologia*, 1999; 42:579–588.

Ulrich, P. and Zhang, X. "Pharmacological reversal of advanced glycation end–product–mediated protein crosslinking", *Diabetologia*, 1997; 40:S157–S159.

van Boekel, M. et al., "Glycation of human serum albumin: inhibition by Diclofenac", *Biochimica et Biophysica Acta*, 1992; 1120:201–204.

Vasan, S. et al. "An agent cleaving glucose–derived protein crosslinks in vitro and in vivo", *Nature*, Jul. 18, 1996; 382:275–278.

Wolffenbuttel, B. et al. "Breakers of advanced glycation end products restore large artery properties in experimental diabetes", *Proc. Natl. Acad. Sci. USA*, Apr. 1998; 95:4630–4634.

BREAKERS OF ADVANCED GLYCATION ENDPRODUCTS

CROSS REFERENCE TO RELATED APPLICATIONS

The present invention is a continuation-in-part of application Ser. No. 09/800,976, filed Mar. 8, 2001, which is a continuation-in-part of application Ser. No. 09/543,703, filed Apr. 5, 2000, which is related to provisional application Serial No. 60/127,835, filed Apr. 5, 1999, and the present application is a continuation-in-part of application Ser. No. 09/626,859, filed Jul. 27, 2000, which is a continuation-in-part of application Ser. No. 09/543,703 filed Apr. 5, 2000 which is related to application Ser. No. 60/127,835 filed Apr. 5, 1999, and the present application is a continuation-in-part of application Ser. No. 09/559,913 filed Apr. 28, 2000 which is related to application Ser. No. 60/131,675 filed Apr. 29, 1999, all of which are incorporated herein by reference and all of which are claimed as priority documents.

BACKGROUND OF THE INVENTION

Glucose and other reducing sugars react and bind covalently to proteins, lipoproteins and DNA by a process known as non-enzymatic glycation. Glucose latches onto tissue proteins by coupling its carbonyl group to a side-chain amino group such as that found on lysine. Over time, these adducts form structures called advanced glycation endproducts (AGEs) (protein-aging). These cross-linked proteins stiffen connective tissue and lead to tissue damage in the kidney, retina, vascular wall and nerves. The formation of AGEs on long-lived connective tissue accounts for the increase in collagen cross-linking that accompanies normal aging which occurs at an accelerated rate in diabetes.

The publications and other materials used herein to illuminate the background of the invention or provide additional details respecting the practice, are incorporated by reference, and for convenience are respectively grouped in the appended List of References.

Advanced glycation endproducts (AGEs) have been implicated in the pathogenesis of a variety of debilitating diseases such as diabetes, atherosclerosis, Alzheimer's and rheumatoid arthritis, as well as in the normal aging process. Most recent researchers confirm a significant role of the accumulation of AGE cross-links in promoting the decreased cardiovascular compliance of aging (Asif et al., 2000; Vaitkevicius et al., 2001). The process of AGE formation on arterial wall matrix proteins may be related to the development of atherosclerosis in many different ways, such as generation of free radicals (ROS) during the glycation process, inhibition of a normal network formation in collagen by AGE accumulation (Brownlee, 1994), and increased adhesion of monocytes (Gilcrease and Hoover, 1992).

The hallmark Diabetes Control and Complications Trial (DCCT) demonstrated that normalization of blood glucose control by intensive insulin therapy reduces the risk of development of diabetic complications (Diabetes Control and Complications Trial Research Group, 1993). However, intensive insulin therapy neither prevents nor cures complications. Thus, a large number of patients still are prone to develop vascular complications, and additional pharmacological approaches to prevent these complications are desirable.

More recently, several promising therapeutic drugs that could inhibit or break the AGE crosslinks in tissues and cells, and thus prevent these complications, have been reported. Both inhibitors of AGE formation and AGE-breakers not only may have a beneficial effect in reducing these complications, AGE-breakers may cure the disease by removing AGEs from damaged tissues and cells.

Aminoguanidine is a prototype of "glycation inhibitors". These inhibitors may find therapeutic use in preventing diabetic complications and in delaying normal aging. In addition to aminoguanidine, a large number of much more potent inhibitor compounds have been introduced by us and others recently (Rahbar et al., 1999; Rahbar et al., 2000a; Rahbar et al., 2000b; Kochakian et al., 1996; Khalifah et al., 1999; Soulis et al., 1999; Forbes et al., 2001).

Investigation for selectively cleaving and severing the existing AGE-derived cross-links on tissue proteins by pharmacological strategies has been started more recently. N-phenacylthiazolium bromide (PTB) and ALT 711 have been reported to break AGE cross-links in vitro and in vivo. The introduction of PTB, the first AGE-breaker which was introduced in 1996, generated excitement among the researchers in this field. However, PTB was used at non-physiological concentrations (10–30 mM), and was observed to degrade rapidly in vitro (Thomalley and Minhas, 1999). Additionally, contrasting results were observed on diabetic rats treated with PTB used at the same concentration of 10 mg/kg daily (Cooper et al., 2000; Oturai et al., 2000). Although the more stable PTB derivative ALT711 has demonstrated AGE-breaking activities both in vitro and in vivo (Vasan et al., 1996; Rahbar et al., 1999), a recent report by Yang et al. (2000) found that ALT711 was not effective in cleaving crosslinks formed in skin and tail collagen of diabetic rats.

The Diabetes Control and Complications Trial (DCCT), has identified hyperglycemia as the main risk-factor for the development of diabetic complications (Diabetes Control and Complications Trial Research Group, 1993). Ever increasing evidence identifies the formation of advanced glycation endproducts (AGEs) as the major pathogenic link between hyperglycemia and the long-term complications of diabetes, namely nephropathy, neuropathy and retinopathy (Makita et al., 1994; Koschinsky et al., 1997; Makita et al., 1993; Bucala et al., 1994; Bailey et al., 1998).

Nonenzymatic glycation is a complex series of reactions between reducing sugars and amino groups of proteins, lipids and DNA, which lead to browning, fluorescence, and cross-linking (Bucala and Cerami, 1992; Bucala et al., 1993; Bucala et al., 1984). The reaction is initiated with the reversible formation of a Schiff's base, which undergoes a rearrangement to form a stable Amadori product. Both the Schiff's base and Amadori product further undergo a series of reactions through dicarbonyl intermediates to form advanced glycation endproducts (AGEs).

In human diabetic patients and in animal models of diabetes, these nonenzymatic reactions are accelerated and cause accumulation of glycation products on long-lived structural proteins such as collagen, fibronectin, tubulin, lens crystallin, myelin, laminin and actin, and in addition on several other important biological molecules such as hemoglobin, albumin, LDL-associated lipids and apoprotein. Most recent reports indicate that glycation inactivates metabolic enzymes (Yan and Harding, 1999). The structural and functional integrity of the affected molecules, which often have major roles in cellular functions, become perturbed by these modifications with severe consequences on affected organs such as kidney, eye, nerve, and microvascular vessels (Boel et al., 1995; Silbiger et al., 1993; Vlassara et al., 1995; Horie et al., 1997; Matsumoto et al., 1997; Soulis-Liparota et al., 1991; Bucala, 1997; Bucala and Rahbar, 1998; Park et al., 1998). Recent reports indicate glycation to affect metabolic enzymes, high-density lipoproteins and IgG molecules (Yan and Harding, 1999; Lapolla et al., 2000; Lucey et al., 2000; Schalkwijk et al., 1998; Hedrick et al., 2000). The glycation-induced change of immunoglobin G is of particular interest. Recent reports of glycation of Fab fragment of IgG in diabetic patients suggest that immune deficiency observed in these patients may be explained by this phenomenon (Lapolla et al., 2000). Furthermore, an association between IgM response to IgG damaged by glycation and disease activity in rheumatoid arthritis have been reported recently (Lucey et al., 2000). Also, impairment of high-density lipoprotein function by glycation has been reported recently (Hedrick et al., 2000).

Direct evidence indicating the contribution of AGEs in the progression of diabetic complications in different lesions of the kidneys, the rat lens, and in atherosclerosis has been recently reported (Vlassara et al., 1995; Horie et al., 1997; Matsumoto et al., 1997; Soulis-Liparota et al., 1991; Bucala, 1997; Bucala and Rahbar, 1998; Park et al., 1998). Several lines of evidence indicate the increase in reactive carbonyl intermediates (methylglyoxal, glyoxal, 3-deoxyglucosone, malondialdehyde, and hydroxynonenal) is the consequence of hyperglycemia in diabetes. This "carbonyl stress" leads to increased modification of proteins and lipids, followed by "oxidative stress" and tissue damage (Baynes and Thorpe, 1999; Onorato et al., 1999; McLellan et al., 1994).

Methylglyoxal (MG) has recently received considerable attention as a common mediator to form AGEs. In patients with both insulin-dependent and non-insulin dependent diabetes, the concentration of MG was found to be increased 2–6 fold (Phillips and Thornalley, 1993; Beisswenger et al., 1998). Furthermore, MG has been found not only as the most reactive dicarbonyl AGE-intermediate in cross-linking of proteins, a recent report has found MG to generate reactive oxygen species (ROS) (free radicals) in the course of glycation reactions (Yim et al., 1995).

An intricate relationship between glycation reactions and "oxidative stress" has been postulated (Baynes and Thorpe, 1999). Nature has devised several humoral and cellular defense mechanisms to protect tissues from deleterious effects of "carbonyl stress" and accumulation of AGEs. These include the glyoxylase system (I and II) and aldose reductase catalyze the deglycation of methylglyoxal (MG), the most common reactive intermediate of AGEs (Phillips and Thornalley, 1993; Beisswenger et al., 1998; Yim et al., 1995), to D-lactate. Additionally, a novel class of enzymes found in Aspergillus, called amadoriases, was found to catalyze the deglycation of Amadori products (Takahashi et al., 1997). Furthermore, several AGE-receptors have been characterized on the surface membranes of monocyte, macrophage, endothelial, mesangial and hepatic cells. One of these receptors, RAGE, a member of the immunoglobulin superfamily, has been found to have a wide distribution in tissues (Schmidt et al., 1994; Yan et al., 1997). MG binds to and irreversibly modifies arginine and lysine residues in proteins. MG modified proteins have been found as ligands for the AGE receptor (Westwood et al., 1997) indicating that MG modified proteins are analogous (Schalkwijk et al., 1998) to those found in AGEs. The discovery of various natural defense mechanisms against glycation and AGE formation suggests an important role of AGEs in the pathogenesis of vascular and peripheral nerve damage in diabetes. Most recently, the effects of MG on LDL have been characterized in vivo and in vitro (Bucala et al., 1993).

Lipid peroxidation of polyunsaturated fatty acids (PUFA), such as arachidonate, also yield carbonyl compounds. Some are identical to those formed from carbohydrates (Al-Abed et al., 1996), such as MG and glyoxal (GO), and others are characteristic of lipid, such as malondialdehyde (MDA) and 4-hydroxynonenal (HNE) (Requena et al., 1997). The latter of the carbonyl compounds produce lipoxidation products (Al-Abed et al., 1996; Requena et al., 1997). A recent report emphasizes the importance of lipid-derived MDA in the cross-linking of modified collagen and in diabetes mellitus (Slatter et al., 2000). A number of fluorescent and non-fluorescent AGE compounds that are involved in protein cross-linking have been characterized (Baynes and Thorpe, 1999) (see Table 1). In addition to glucose derived AGE-protein cross-links, AGE cross-linking also occurs between tissue proteins and AGE-containing peptide fragments formed from AGE-protein digestion and turnover. These reactive AGE-peptides, now called glycotoxins, are normally cleared by the kidneys. In diabetic patients, these glycotoxins react with the serum proteins and are a source for widespread tissue damage (Schmidt et al., 1994). However, detailed information on the chemical nature of the cross-link structures remains unknown. The cross-linking structures characterized to date (Table 1), on the basis of chemical and spectroscopic analyses, constitute only a small fraction of the AGE-cross-links which occur in vivo, with the major cross-linking structure(s) still unknown. Recently, a novel acid-labile AGE-structure, N-omega-carboxymethylarginine (CMA), has been identified by enzymatic hydrolysis of collagen, and its concentration was found to be 100 times greater than the concentration of pentosidine (Iijima et al., 2000), and has been assumed to be a major AGE-cross-linking structure (Yan et al., 1997).

TABLE 1

CURRENT LIST OF AGEs IDENTIFIED IN TISSUE PROTEINS AND IN VITRO GLYCATION EXPERIMENTS (Baynes and Thorpe, 1999)

Carboxymethyllysine (CML)
Carboxyethyllysine (CEL)
Carboxymethylarginine (CMA)
Pentosidine
Pyralline
Crosslines (A, B)
Glyoxallysine dimers (GOLD), Imidazolium salts
Methylglyoxal-lysine dimers (MOLD), Imidazolium salts
Imidazolones and dehydroimidazolones { 3-Deoxyglucosone-Arginine MGO-Arginine
Pyrrolopyrridinium
Arginine - Lysine dimer (ALS)
Arginine Pyridinium
Cypentodine
Piperidinedinone enol
Vesperlysine
MRX

SUMMARY OF THE INVENTION

Seven compounds have been found which are active in breaking AGE-protein cross-links. These compounds are: 1,4-benzene-bis[4-methyleneaminophenoxyisobutyric acid] (LR 102); 4-[(3,5-dichlorophenylureidophenoxyisobutyryl]-4-aminobenzoic acid (LR99); L-bis-[4-(4-chlorobenzamidophenoxyisobutyryl)cystine] (LR20); 4-(3, 5-dichlorophenylureido)phenoxyisobutyryl-1-amidocyclohexane-1-carboxylic acid (LR23); methylene bis [4,4'-(2-chlorophenylureidophenoxyisobutyric acid)] (LR90); 5-aminosalicylic acid (5-ASA) (also referred to herein as SMR-5); and metformin (also referred to herein as SMR-12).

In one aspect of the invention, these AGE-breaking compounds are used to break glycation endproducts or crosslinked proteins in an organism by administering to an organism an effective amount of one or more of the AGE-breakers.

In a second aspect of the invention, the deleterious effects of aging in an organism are reversed by administering an effective amount of an AGE-breaker to the organism.

In a third aspect of the invention, complications resulting from diabetes in an organism are reversed by administration of an effective amount of an AGE-breaker to the organism.

In further aspects of the invention, the progress of disease in a patient, wherein the disease can include rheumatoid arthritis, Alzheimer's disease, uremia, neurotoxicity, or atherosclerosis, is reversed by administration of an effective amount of an AGE-breaker to the patient.

BRIEF DESCRIPTION OF THE FIGURES

FIG. 5A shows solubility in weak acid, FIG. 5B shows the results with pepsin digestion, and FIG. 5C shows the results with papain digestion. Values are means ±S.D. of 2–3 collagen samples. P values were calculated using unpaired Student's t-test. For each figure * indicates P<0.05 vs. non-diabetic control and ** indicates P<0.05 vs. diabetic control.

DETAILED DESCRIPTION OF THE INVENTION

We have reported a new class of compounds, aryl (and heterocyclic) ureido and aryl (and heterocyclic) carboxamido phenoxyisobutyric acids, as inhibitors of glycation and AGE formation (Rahbar et al., 1999; Rahbar et al., 2000a). A number of highly effective inhibitors were among the 92 compounds tested (Rahbar et al., 1999; Rahbar et al., 2000a). These were selected for in vivo experimentation in streptozotocin (STZ) induced diabetic rats. Recent discoveries of novel compounds, such as phenacylthiazolium bromide (PTB) (Vasan et al., 1996) and ALT 711 (Wolffenbuttel et al., 1998), which are able to cleave selectively the established AGE-protein cross-links in vitro and in vivo, have been exciting (Cooper et al., 2000). Furthermore, ALT 711 was reported to reverse the age-related increase of myocardial stiffness in vivo in aging dogs and monkeys (Asif et al., 2000; Vaitkevicius et al., 2001). Disclosed here are the results of an investigation of AGE-breaking properties of a number of compounds we have recently developed as potent inhibitors of glycation and AGE-formation (Rahbar et al., 1999; Rahbar et al., 2000a). Using a specific ELISA technique and other in vitro assays for screening our compounds, seven compounds have been found to be powerful AGE-cross-link breakers. These compounds are: 1,4-benzene-bis[4-methyleneaminophenoxyisobutyric acid] (LR102); 4-[(3,5-dichlorophenylureidophenoxyisobutyryl]-4-aminobenzoic acid (LR99); L-bis-[4-(4-chlorobenzamidophenoxy isobutyryl) cystine (LR20); 4-(3, 5-dichlorophenylureido)-phenoxyisobutyryl-1-amidocyclohexane-l-carboxylic acid (LR23); methylene bis [4,4'-(2-chlorophenylureidophenoxyisobutyric acid)] (LR90); 1,1-dimethylbiguanide (metformin); and 5-aminosalicylic acid (5-ASA). The structures of LR20, LR23, LR90, LR99 and LR102 are:

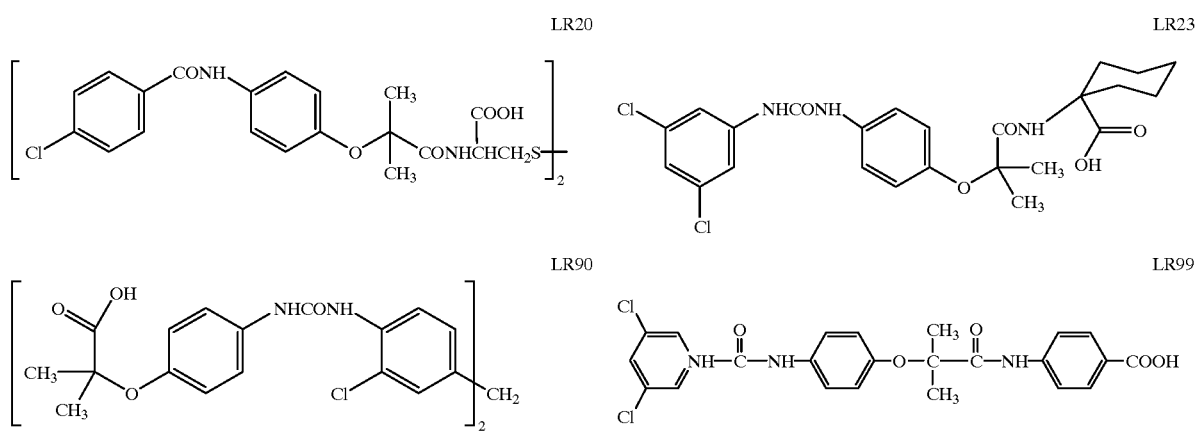

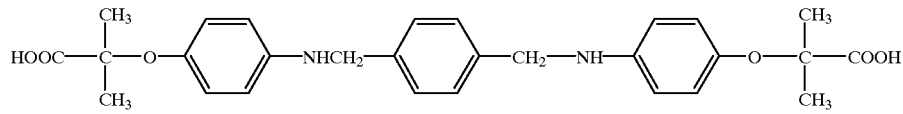

LR102

Figure 1A:
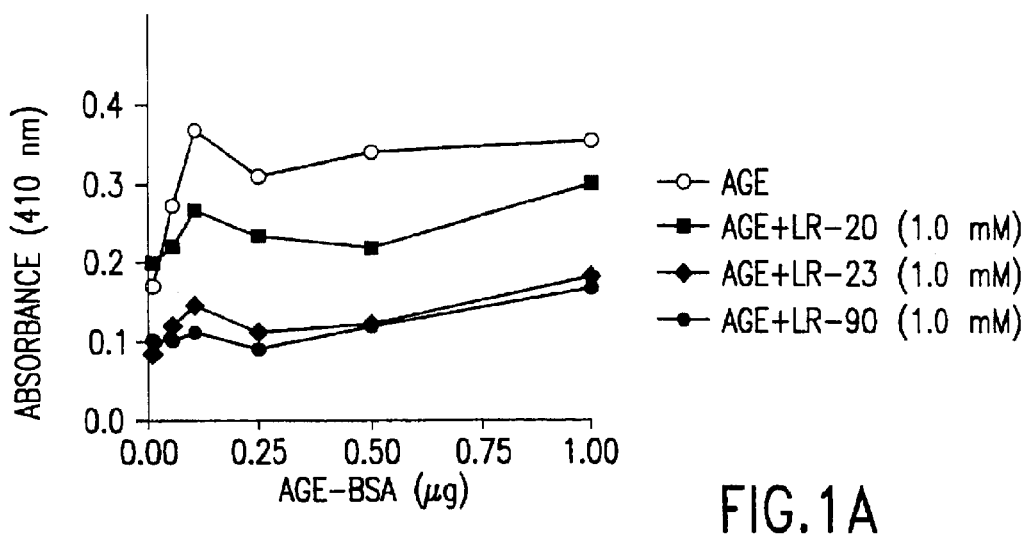
FIG. 1A shows the cleavage of cross-linked collagen-AGE-BSA by LR20, LR23 and LR90. AGE represents collagen-AGE-BSA in the absence of any AGE-breaker.
Figure 1B:
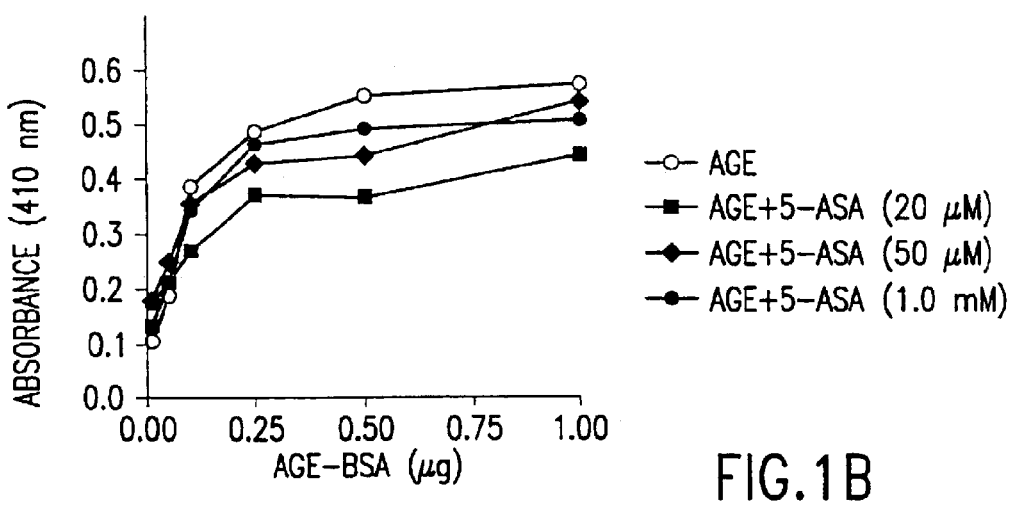
FIG. 1B shows the dose dependent AGE-breaking activity of 5-ASA by measuring cleavage of cross-linked collagen-AGE-BSA. AGE represents collagen-AGE-BSA in the absence of 5-ASA.
Figure 1C:
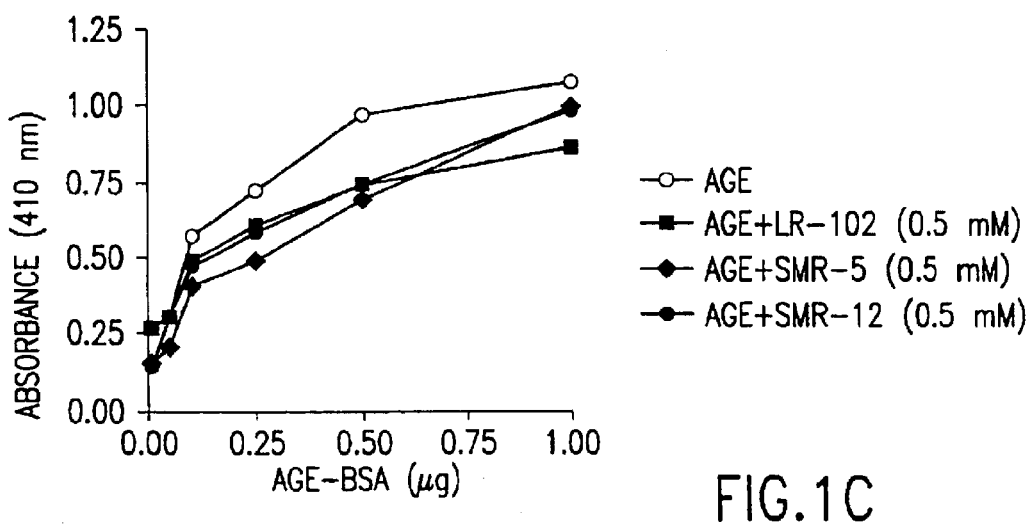
FIG. 1C shows the cleavage of cross-linked collagen-AGE-BSA by LR102, 5-ASA (SMR-5), and metformin (SMR-12). AGE represents collagen-AGE-BSA in the absence of any AGE-breaker.
Figure 2A:
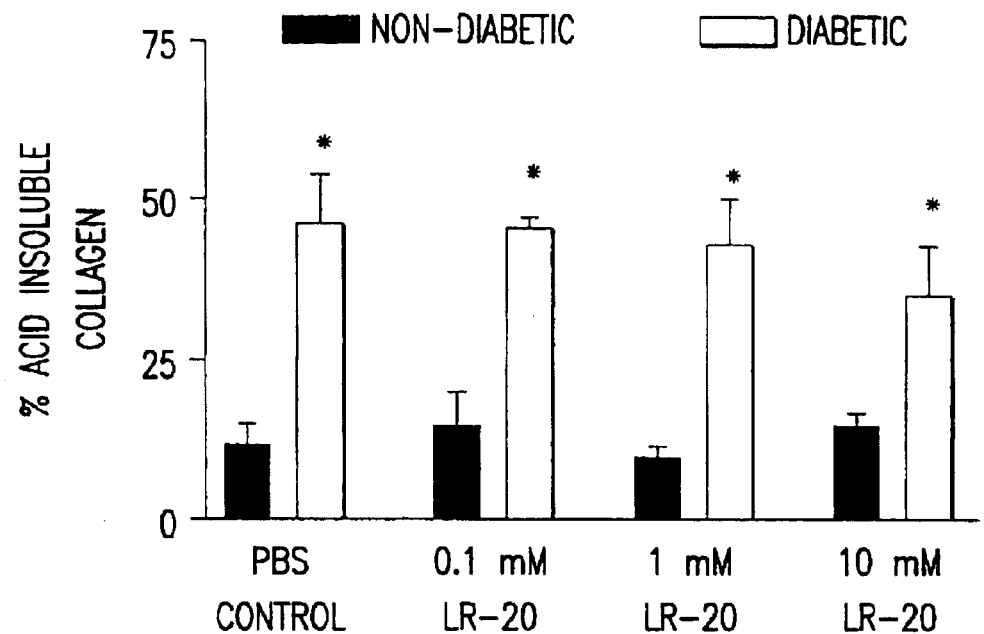
FIGS. 2A–D show the solubility of collagen treated with novel AGE-breakers (LR20, LR23, LR99 and LR102) in weak acetic acid. Values are means ±S.D. of 2–3 collagen samples. P values were calculated using unpaired Student's t-test. For each figure * indicates P<0.05 vs. non-diabetic control and ** indicates P<0.05 vs. diabetic control.
Figure 2B:
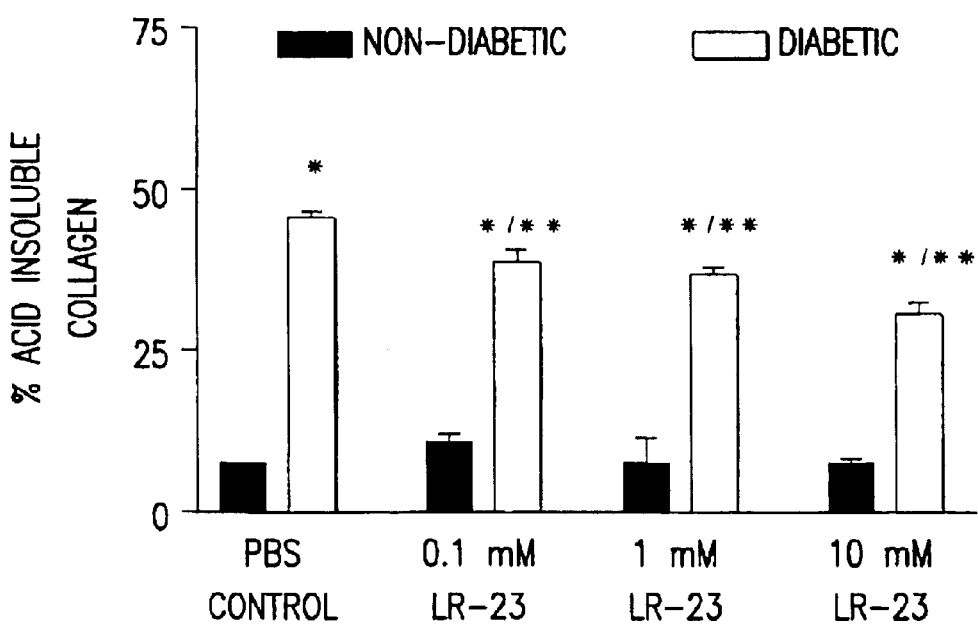
Figure 2C:
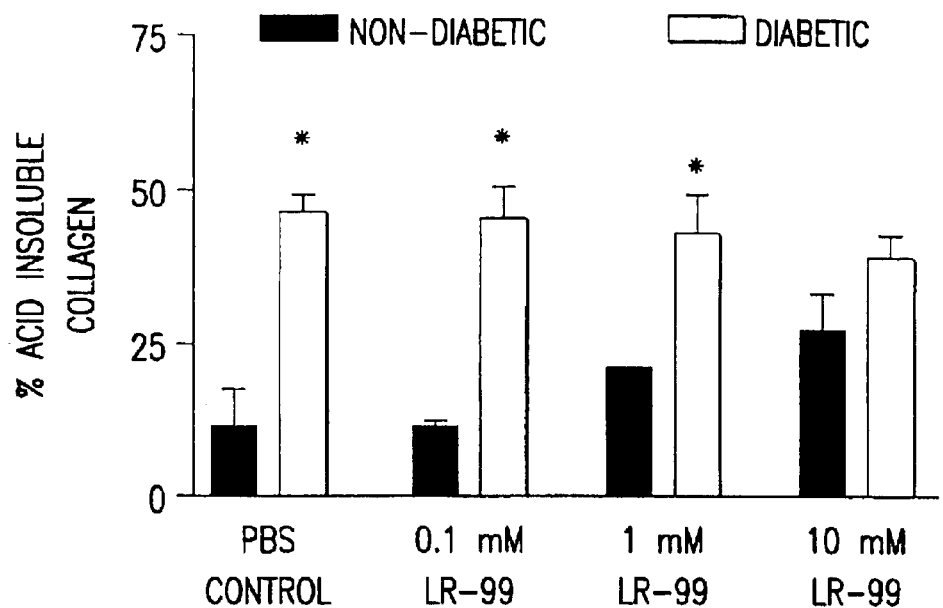
Figure 2D:
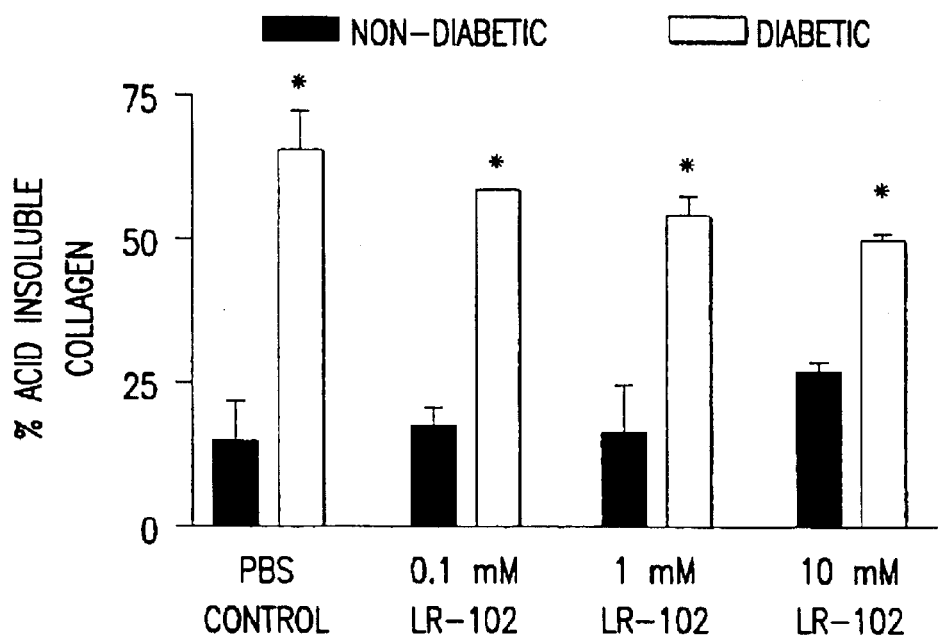
Figure 3A:
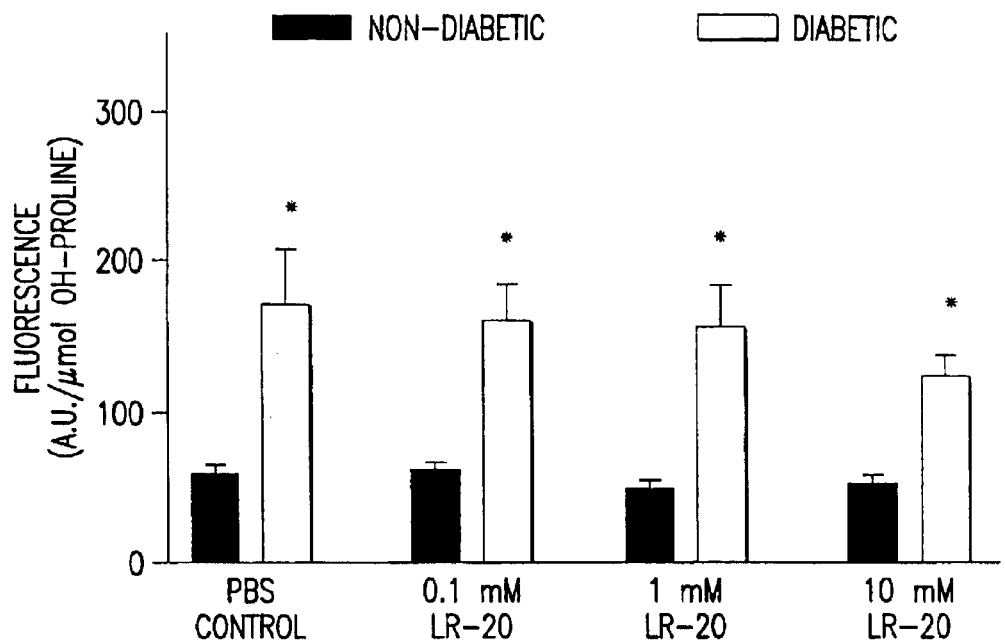
FIGS. 3A–D show the results of pepsin digestion of collagen treated with novel AGE-breakers (LR20, LR23, LR99 and LR102). Values are means ±S.D. of 2–3 collagen samples. P values were calculated using unpaired Student's t-test. For each figure * indicates P<0.05 vs. non-diabetic control and **indicates P<0.05 vs. diabetic control.
Figure 3B:
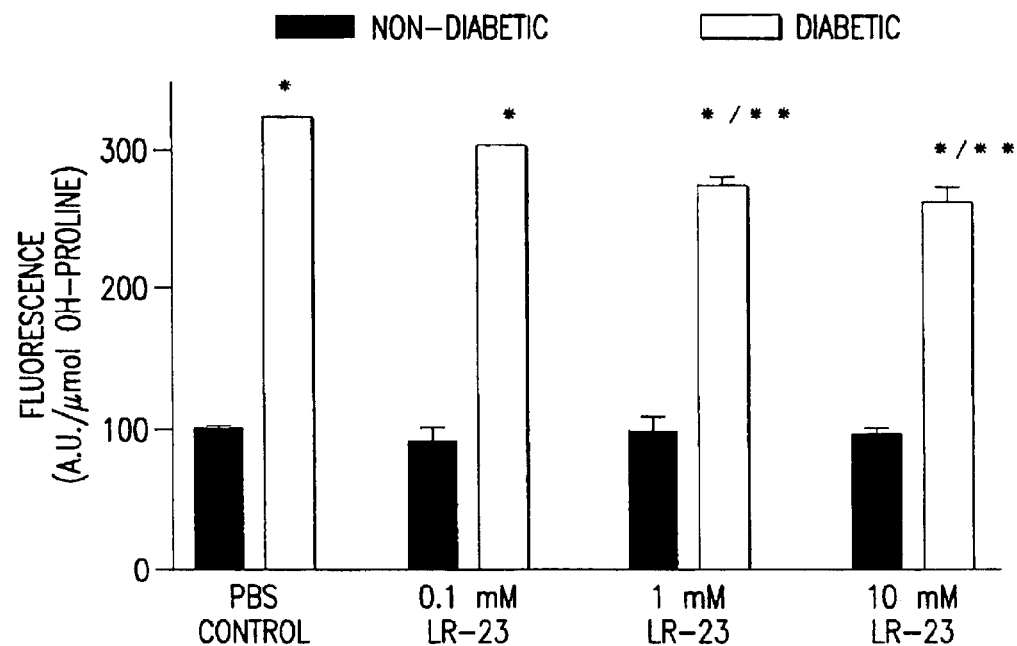
Figure 3C:
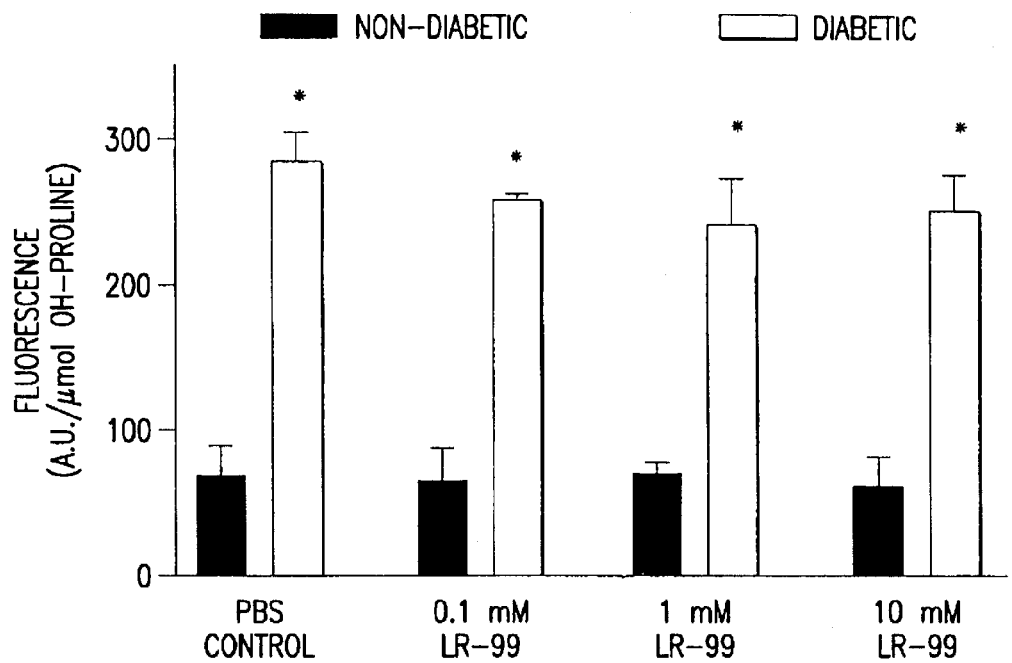
Figure 3D:
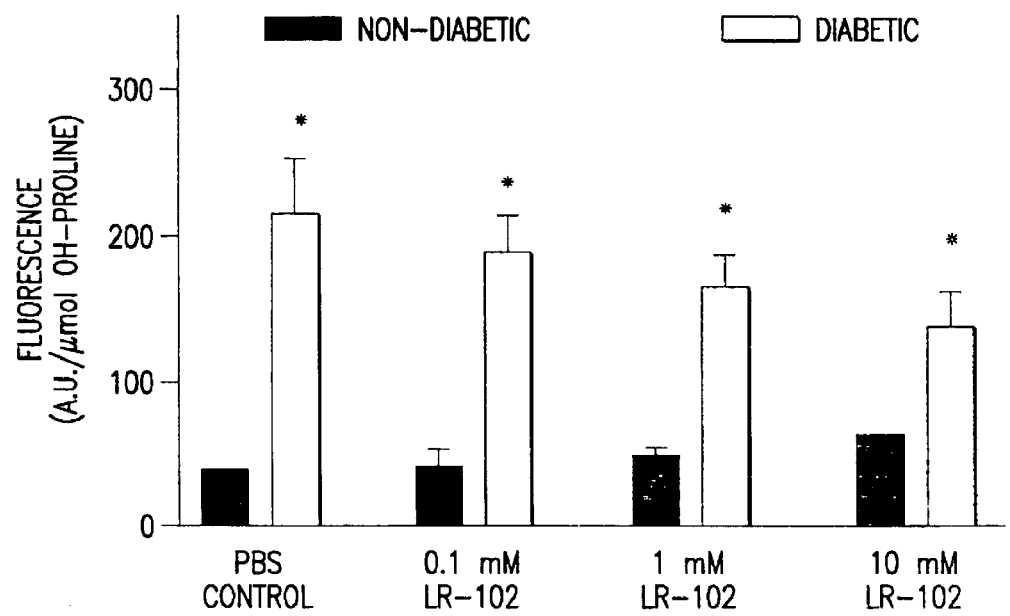
Figure 4A:
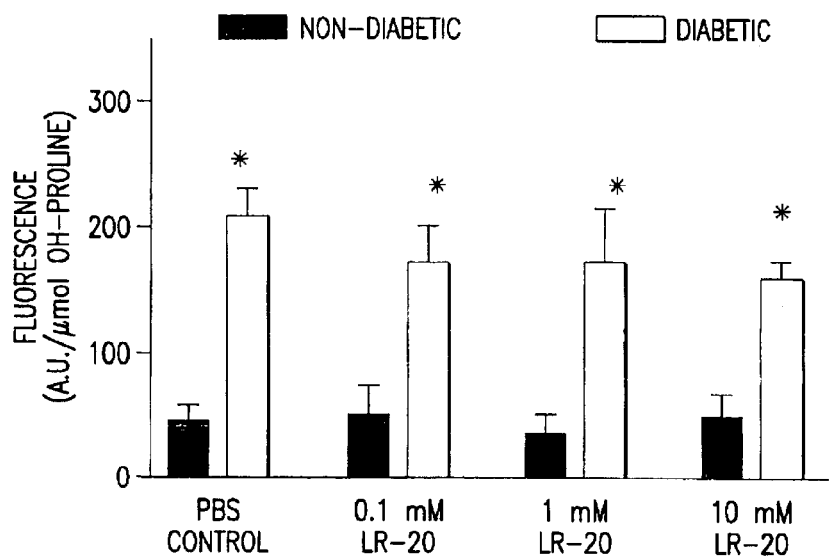
FIGS. 4A–D show the results of papain digestion of collagen treated with novel AGE-breakers (LR20, LR23, LR99 and LR102). Values are means ±S.D. of 2–3 collagen samples. P values were calculated using unpaired Student's t-test. For each figure * indicates P<0.05 vs. non-diabetic control and ** indicates P<0.05 vs. diabetic control.
Figure 4B:
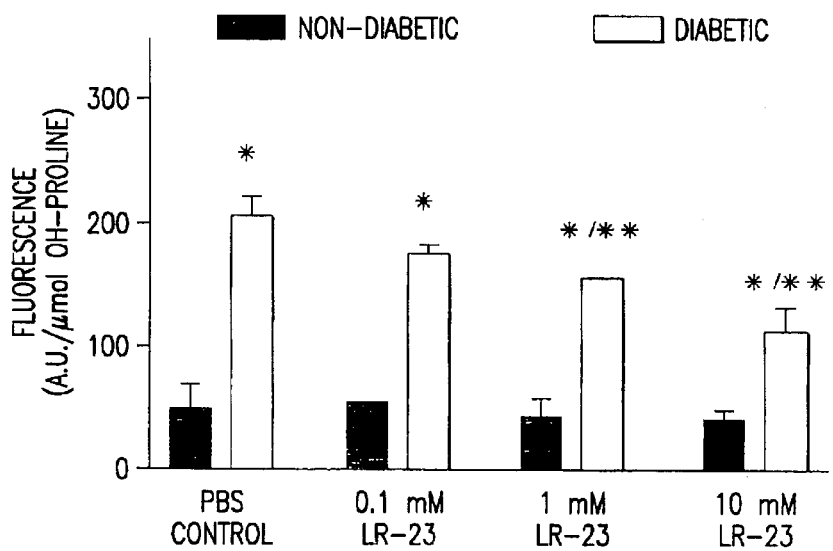
Figure 4C:
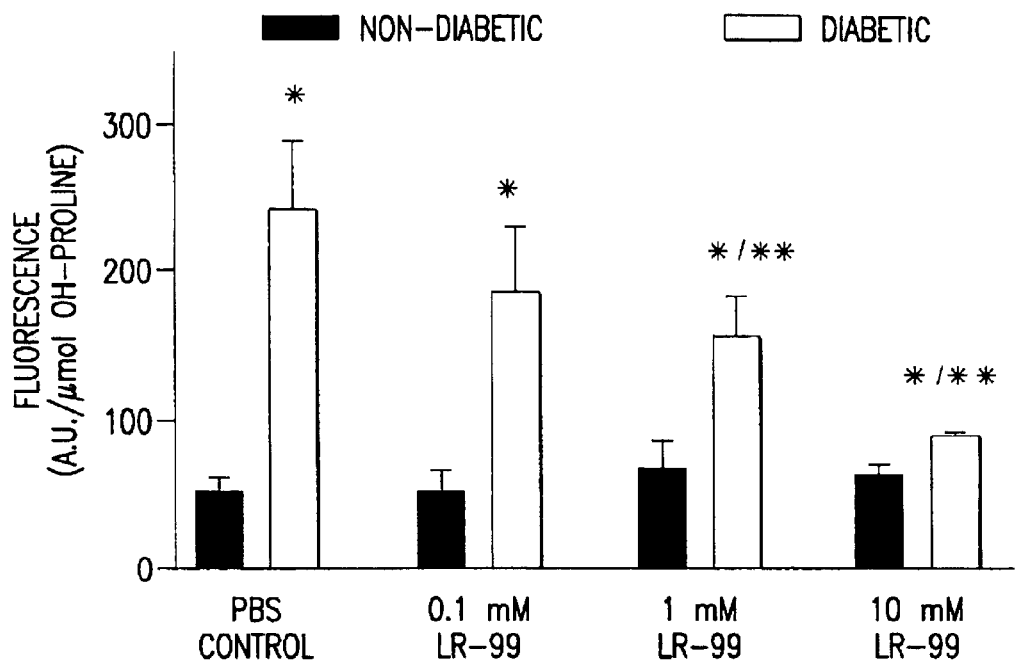
Figure 4D:
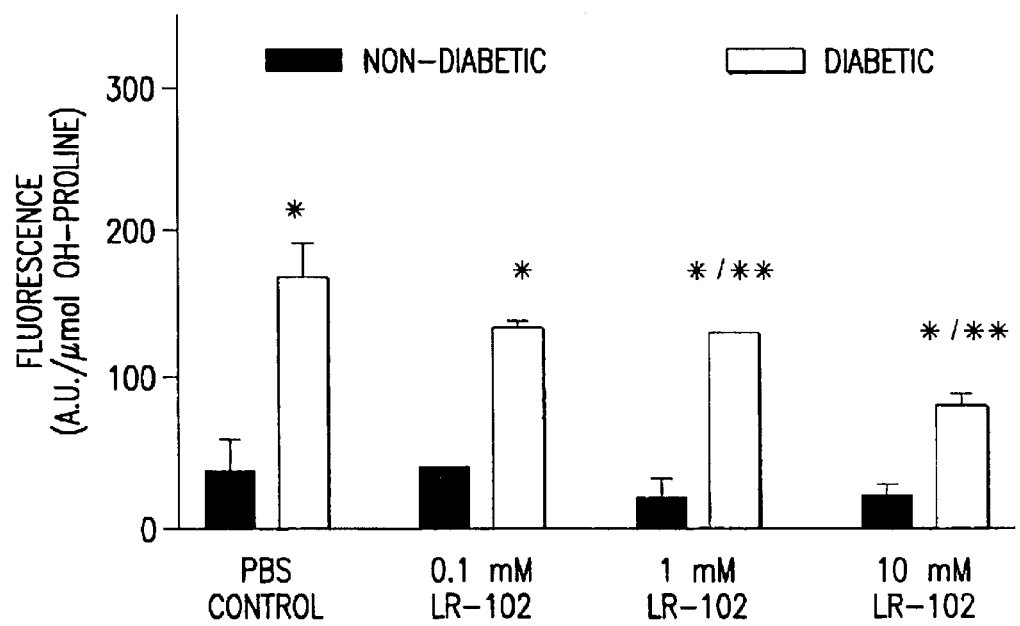

As described in the Examples below, compounds LR20, LR23, LR90, LR99 and LR102 in this study were each used at 0.1–10 mM final concentration and were very effective AGE-breakers as demonstrated in FIGS. 1A and 1C. 5-ASA was used at 20 μM, 50 μM and 1 mM and demonstrated dose dependent AGE-breaking activities as shown in FIG. 1B. This characteristic of 5-ASA may be one of the reasons this drug is effective in the treatment of "ulceritis colitis" and Crohn disease. Furthermore, this drug may have beneficial effects in reversing AGE-cross-links in rheumatoid arthritis where accumulation of AGE in collagen and an immunological response to IgG damaged by glyoxidation (AGE-IgG) have been reported recently (Lucey et al., 2000). Finally, 5-ASA may have some effects on reducing damage of the β-amyloid contents of Alzheimer plaques.

Metfonnin, a highly popular drug for the treatment of Type 2 diabetes, was found by us to be a potent inhibitor of glycation (Rahbar et al., 2000b). In the Examples below evidence is presented that metformin is also a moderate AGE-breaker.

The mechanism of action of our AGE-breaker compounds is yet to be discovered. However, since these compounds release BSA from the preformed AGE-BSA-Collagen complex as detected immunochemically by ELISA, we assume these AGE-breakers are able to chemically cleave α-diketones by breaking the chemical bond between the carbonyl groups, similar to the PTB mechanism of action (Ulrich and Zhang, 1997).

The present invention is further detailed in the following Examples, which are offered by way of illustration and are not intended to limit the invention in any manner. Standard techniques well known in the art or the techniques specifically described below are utilized.

EXAMPLE 1

Compounds and Materials

LR20, LR23, LR90, LR99 and LR102 were synthesized in our laboratory. These compounds are easily synthesized by those of skill in the art. These are among the 102 compounds we have developed as inhibitors of glycation and AGE formation (Rahbar et al., 1999; Rahbar et al., 2000a). Metformin (1,1-dimethylbiguanide) and 5-aminosalicylic acid (5-ASA) were purchased from Sigma.

Rat tail-tendon-collagen coated 96 well microtiter plates were purchased from Biocoat (Collaborative Research, Bedford, Mass.) and used according to the manufacturer's instructions. Streptozotocin, rabbit polyclonal anti-BSA antibody, rat-tail-collagen (type VII, acid soluble), bovine serum albumin, glucose, human IgG, rabbit-anti-rat IgG, anti-human IgG, methylglyoxal, pepsin, papain, 1-propanol, chloramine-T trihydrate, EDTA, PMSF, iodoacetamide, benzamidine hydrochloride, p-dimethylamino-benzaldehyde, trans-4-hydroxyproline (crystalline), Thioflavin-T (ThT) and Congo Red (CR) were obtained from Sigma Chemical co. (St. Louis, Mo.). The horseradish peroxidase-linked goat anti-rabbit IgG and hydrogen peroxide substrate ABTS (2,2'-azino-di-3-ethylbenzthiazoline sulfonic acid) as chromogen was purchased from Zymed (San Francisco, Calif.). Perchloric acid (70% ACS), glacial acetic acid (99.5%, ASA) and 12 N hydrochloric acid were from J. T. Baker (Phillipsburg, N.J.). β-amyloid (1–40) peptide was from Bachem (Torrance, Calif.). Amicon filters (cut-off 10,000 Da) were obtained from Amicon (Beverly, Mass.). Spectra/Por CE dialysis membrane (molecular cut-off 1000 Da) was from Spectrum Inc. (Houston, Tex.). All other reagents used were of analytical grade.

EXAMPLE 2

Evaluation of Cleavage of Glycated BSA by AGE-breaker Compounds

In vitro evaluation of the ability of the AGE-breaker compounds to cleave and break cross-linking of glycated BSA (AGE-BSA) (prepared as described (Rahbar et al., 1999)) to the rat-tail-tendon-collagen was by a special ELISA (Vasan et al., 1996). The rat-tail-tendon-collagen coated plates were first blocked first with 300 μL of Superblock blocking buffer (Pierce Chemicals, Rockford, Ill.) for one hour. The blocking solution was removed from the wells by washing the plates twice with PBS-0.05% Tween 20 (PBS-T) using a Dynatech ELISA-plate washer. Cross-linking of various concentrations of AGE-BSA (0, 0.01, 0.05, 0.1, 0.25, 0.50, and 1.0 μg per well) to rat-tail-collagen coated plates was performed without the testing compound, and the plates were incubated for 5 hours at 37° C. After washing the wells three times with PBS-T to remove the unattached AGE-BSA, test concentrations of the compound (50 μL/well) dissolved in PBS were added to wells in triplicate and incubation continued at 37° C. overnight. After washing with PBS-T, the amount of BSA remaining attached to the tail collagen plate was then quantified by addition of rabbit anti-BSA polyclonal antibodies (50 μL/well) for 1 hour at 37° C. The wells were then washed three times with PBS-T and developed with the chromogenic substrate ABTS (100 μL/well). Absorbance was measured at 410 nm in microplate reader (BioRad, Hercules, Calif.).

The percentage breaking activity is calculated by the following formula: $100 \times [(A_{410}, \text{PBS control}) - (A_{410}, \text{AGE-breaker compound})]/[A_{410}, \text{PBS control}]$.

EXAMPLE 3

Disaggregation of β-Amyloid Fibrils in Vitro

AGE-modified β-amyloid peptide, prepared by the incubation of glucose with β-AP (amino acids 1–40, from Bachem, Torrance, Calif.), has been shown to initiate efficiently the aggregation and polymerization of β-AP into amyloid fibrils in vitro.

Originally this assay was used for PTB (Al-Abed et al., 1999) and showed that PTB at 20 mM concentration disaggregates β-amyloid fibrils that have been aggregated in this manner. In the original version of this assay, AGE-β-amyloid had to be radioiodinated and then dialyzed to remove the unincorporated radioiodine $^{125}$I and separated by SDS-PAGE in a 4–10% gradient gel which makes this assay very cumbersome.

In a new version of this assay, Bucala and Callaway (Bucala, personal communication; Tjernberg et al., 1999) have proposed the following approaches to demonstrate the disaggregation of the AGE-β-amyloid peptide by the AGE-breaker compounds. The Thioflavin T (ThT) fluorescence assay and Congo Red binding assay are based on the fact that Congo Red and ThT undergo characteristic spectral alteration on binding to a variety of amyloid fibrils (β-sheet conformation) that do not occur on binding to the precursor polypeptides and monomers. Both dyes have been adapted to in vitro measurements of amyloid fibril formation and quantification. ThT binding to β-amyloids gives rise to a large fluorescence excitation spectral shift that allows selective excitation of the amyloid fibril bound ThT (Tjernberg et al., 1999). In the present study, we have investigated the disaggregation of both native (unmodified) and glycated β-amyloid (1–40) peptide by the AGE-breaker compounds introduced here.

EXAMPLE 4

Preparation of glycated β-amyloid (AGE-Amyloid) (Loske et al., 2000; Munch et al. 1997)

Stock solutions of peptide were dissolved in deionized water at a concentration of 1 mg/mL. For AGE crosslinking experiments, they were incubated in 4 mL polypropylene tubes at a concentration of 250 μg/mL (60 μM) and 50 mM glucose in 50 mM sodium phosphate buffer, pH 7.9, at 50° C. in the dark for 5 days. Sodium azide (0.01% w/v) was added to prevent microbiological growth. In long-term experiments, water was added every 12 hours to compensate for solvent evaporation. AGE-β-amyloid was then dialyzed against double-distilled water using Spectra/Por CE dialysis membrane (molecular mass cut off: 1000 Da), and then freeze dried.

EXAMPLE 5

Treatment of AGE-β-amyloid or Native β-amyloid with the AGE-breaker Compound (Asif et al., 2000)

Two sets of experiments were prepared for each compound. Solutions for the first experiment contained 100 μM of β-amyloid in 50 mM Tris-buffered saline (TBS) pH 7.4, and 50 mM of one compound (the drugs were dissolved in DMSO and the solutions were prepared for dilution from this DMSO stock). The second set contained 100 μM of β-amyloid in TBS and 100 μM of one compound. The reactions were incubated at 37° C. for 24 hours without stirring (stagnant assay). Control experiments were prepared accordingly except that no AGE-breaker compounds were added to the tubes. The same protocol was used for both native and glycated β-amyloid peptides.

EXAMPLE 6

Thioflavine T (ThT) Fluorescence Assay (Tjernberg et al., 1999)

The incubated samples are vortexed and 40 μL aliquots are withdrawn and mixed with 960 μL of 10 μM ThT in 10 mM sodium phosphate-buffer. Fluorescence measurements were taken with excitation of 437 nm and emission at 485 nm. Slit widths are set to 5 nm.

EXAMPLE 7

Electron Microscopy

Preparations for the treated and untreated AGE-β-amyloid peptide aggregates were done according to Vasan et al. (1996). These preparations were examined on a transmission electron microscope.

EXAMPLE 8

Cleavage of AGE Cross-links that Form in Vivo

AGE-breaker treatment in vitro can also decrease AGE cross-links that form in situ in rat-tail-tendon collagen of diabetic rats. For this study, diabetes was first induced in male Sprague-Dawley rats (Charles River, Wilmington, Mass.) weighing about 150–175 g by injection of streptozotocin (65 mg/kg, i.p.). Hyperglycemia was then confirmed 1 week later by plasma glucose measurement ($\geq 250$ mg/dL). Thirty-two weeks later, the rats are sacrificed and collagen was isolated from the tail tendon of diabetic and normal controls as described by Kochakian et al. (1996). Tail tendons were dissected free of adhering tissues, washed thoroughly in PBS containing protease inhibitors (1 mM each of EDTA, PMSF, iodoacetamide and benzamidine hydrochloride), patted dry onto a paper towel, rolled into a ball, freeze dried, and stored at −20° C. in sealed containers until used.

EXAMPLE 9

Treatment of Rat Tail Collagen with the AGE-breaker Compound

Representative samples of tail tendon collagen were pulled from its bulk and were cut approximately 20–25 mm in size. The samples were then placed inside 1.5 mL microfuge tubes and suspended with 1 mL of the desired concentration of the AGE-breaker compound in PBS buffer (pH 7.4) containing 0.02 g/L $NaN_3$. Untreated control tubes include tail tendon collagen and PBS buffer only. The tubes were incubated at 37° C. for 24 hours. After incubation, the tubes were centrifuged at 10,000 rpm and the supernatants discarded. The collagen samples were rinsed with PBS, vortexed thoroughly, centrifuged briefly, and the supernatant discarded. This rinsing was repeated twice. On final rinse, the supernatant was discarded and the tubes inverted for one minute for the samples to air dry. These collagen samples were used immediately in the acid solubility and digestion studies.

EXAMPLE 10

Tendon Collagen Solubility in Weak Acid (Sajithlal et al., 1998)

For determination of the amount of acid-insoluble collagen in samples treated and untreated with the AGE-breaker compound, 5 mg aliquots of dried tail-tendon collagen from diabetic and non-diabetic rats, all in duplicates, were added to 2 mL of 0.05 M acetic acid and stirred at 4° C. for 24 hours. The mixture was homogenized in a polytron homogenizer and stirred for an additional 24 hours at 4° C. The suspension was then centrifuged at 9000×g for 60 minutes at 4° C. The collagen in the clear supernatant was defined as the acid soluble collagen, and the gel-like pellet as the acid insoluble collagen. The pellet was lyophilized and weighed, and the percent acid insoluble collagen was calculated as: 100×(lyophilized weight of pellet/original weight of tail tendon collagen). Percent increase in solubility was calculated as: 100×(weight of acid insoluble collagen of untreated diabetic collagen—weight of acid insoluble collagen of treated diabetic collagen)/weight of acid insoluble collagen of untreated diabetic collagen.

EXAMPLE 11

Total Pepsin Digestion Assay (Stefek et al.,2000)

Ten milligrams each of collagen samples from diabetic and non-diabetic tail tendons treated and untreated with the AGE-breaker compounds as described above were vortexed in 1 mL of freshly prepared pepsin (50 μg/mL in 0.5 M acetic acid) for 24 hours at 37° C. Following digestion, the samples were centrifuged at 3,000 rpm for 15 minutes. The clear supernatant containing digested collagen was collected and used for collagen-linked fluorescence. One hundred μL of supernatant were mixed with 900 μL of 200 mM phosphate buffer (pH 7.5), and excitation and emission fluorescence were recorded on a Hitachi F-2000 fluorescence spectrophotometer to determine wavelength values of maximal excitation and emission. Fluorescence of the samples was quantified at 365 nm excitation and 418 nm emission. All fluorescence values were corrected for fluorescence of the pepsin in phosphate buffer and expressed as arbitrary units per micromoles of hydroxyproline content of the collagen sample. The hydroxyproline content of each collagen sample was measured following acid hydrolysis, using a microassay method as described (Creemers et al., 1997). Percent decrease in fluorescence was calculated as: 100× (fluorescence/μmol hydroxyproline of untreated collagen—fluorescence/μmol hydroxyproline treated collagen)/fluorescence/μmol hydroxyproline of untreated collagen.

EXAMPLE 12

Papain Digestibility Assay (Verzijl et al., 2000)

Collagen-linked fluorescence of tail collagen of diabetic and non-diabetic rats treated and untreated with AGE-breaker compounds were measured as follows: about 5 mg of each collagen were digested for 2 hours at 65° C. with 2.5 units/mL of papain in 500 μL of papain buffer (50 mM phosphate buffer (pH 6.5), 2 mM L-cysteine and 2 mM EDTA). Digests were centrifuged at 10,000 rpm for 60 minutes at 4° C., and the supernatant separated from the pellet. Fluorescence measurements at excitation 370 nm and emission 440 nm were performed as described above. Aliquots of the supernatant digests were also subjected to acid hydrolysis followed by hydroxyproline measurements. The results were expressed as fluorescence units per micromole of hydroxyproline content of each sample. Percent decrease in fluorescence was calculated as above.

EXAMPLE 13

Acid Hydrolysis and Hydroxyproline Measurements

Aliquots (100 μL) of the pepsin or papain digests were hydrolyzed with 6 N HCl in 12×35 mm TFE-lined screw cap tubes (Fisher Scientific Co., Pittsburgh, Pa.). The tubes were autoclaved in a steam sterilizer at 250° F. for 3.5 hours. The samples were taken to dryness using a Savant Speed Vac concentrator with heat, and stored at 4° C. until assayed. The dried samples were rehydrated with 200 μL deionized water, and aliquots were assayed for their hydroxyproline content in a 96-well microtiter plate as described by Creemers et al. (1997).

EXAMPLE 14

Determination of Cleavage of IgG-AGE Cross-linked to the Rat RBC Surface Using an Anti-IgG ELISA Assay IgG cross-linked to the RBC surface was determined with an anti-IgG by a modification of the method described by Vasan et al. (1996). Briefly, heparinized blood was drawn from the tail vein in capillary tubes, inverted several times, then centrifuged at 200×g for five minutes at room temperature. RBCs were washed three times with PBS in 0.5 mL microfuge tubes and packed with a final centrifugation at 500×g. Red cells were diluted at 1:10 to 1:100 in Dulbecco's Modified Eagle's Medium that is normal for glucose. Experimental compounds were added at desired concentrations and incubated at 37° C. in a $CO_2$ incubator for 24 hours in sterile conditions. Control incubations contained RBCs and PBS alone. After incubation, RBCs were washed three times in PBS and packed cells diluted 1:200 to 1:500. The RBC suspensions were gently vortexed and 50 μL aliquots added to 450 μL of a polyclonal rabbit anti-rat IgG conjugated to alkaline phosphatase (diluted 1:2500 in PBS). The tubes were then incubated at room temperature for 2 hours, then the RBCs washed three times with PBS, once with Tris-buffered saline (50 mM Tris, pH 8.0), and 0.5 mL to 1 mL p-nitrophenyl phosphate substrate was added (1 mg/mL with 2 mM $Mg^{2+}$ in 0.1 M diethylamine buffered saline, pH 9.5), vortexed and incubated 30 minutes at room temperature. The RBCs were pelleted and the supernatant was read at 410 run in either a conventional spectrometer or an ELISA reader. Blank readings were obtained by incubating tubes without cells.

EXAMPLE 15

Data Analysis

Data are expressed as means ±S.D. or S.E.M. Unpaired students' t-test was used to compare differences between treated samples and control. A P value <0.05 was considered statistically significant.

EXAMPLE 16

Results

The special ELISA method using AGE-BSA to crosslink with collagen-coated microplates is a suitable in vitro assay for rapid screening of crosslink formation and breakage. Using this technique, we observed that many of our previously reported inhibitor compounds are also capable of cleaving and breaking the AGE-BSA-collagen crosslinks (FIGS. 1A–C). Some of the compounds like LR20, LR23 and LR90 are more effective breakers at higher concentrations (FIG. 1A), while others such as LR102, 5-ASA and metformin are more potent at lower concentrations (FIGS. 1B and 1C). We used these compounds to determine their effects on AGE crosslinks that form in vivo in tail tendon collagen of old diabetic rats (32 months old and blood glucose of >25 mmol/L).

Figure 5A:
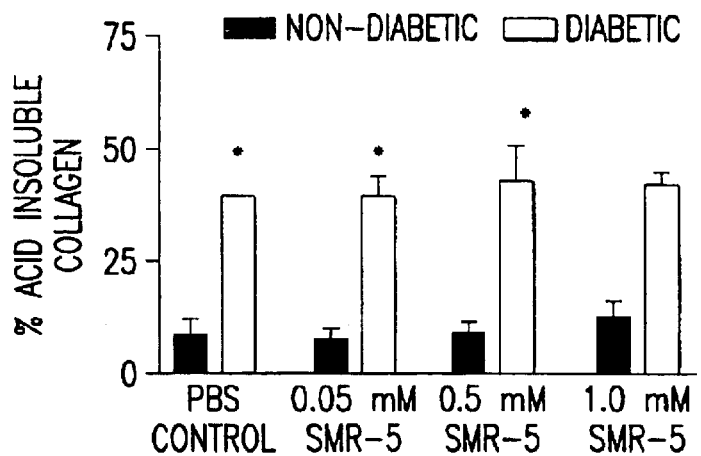
FIGS. 5A–C show the effect of 5-ASA (SMR-5) treatment on rat tail collagen.
Figure 5B:
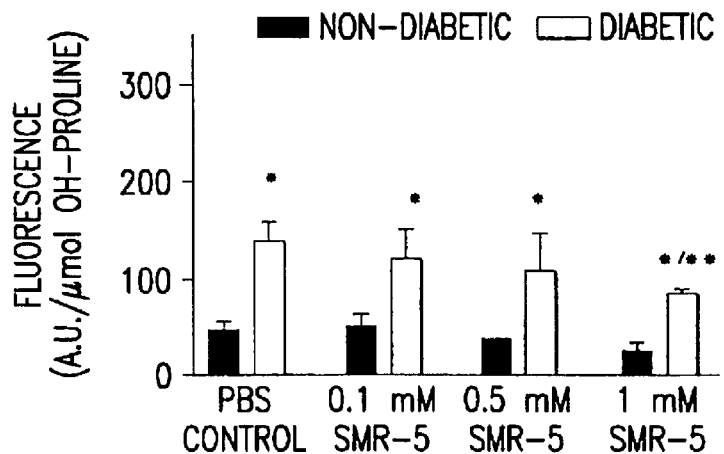
Figure 5C:
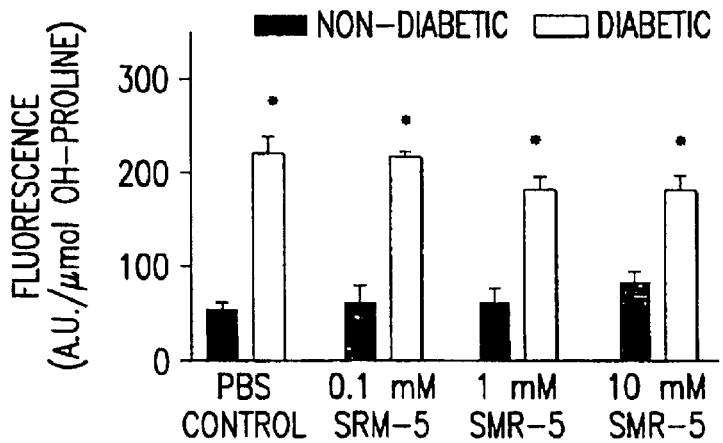

The extent of AGE crosslinking of tail tendon collagen formed in vivo was assessed by acid insolubility and fluorescence measurements (FIGS. 2–5). Table 2 summarizes the effects of these compounds on rat-tail tendon collagen. All three tests produced varying results for the different compounds analyzed. In general, treatment of collagen with the compounds particularly at 1.0 and 10 mM concentrations resulted in increased collagen solubility and reduction of fluorescence associated with AGE crosslinks (FIGS. 2–5, Table 2). In all three tests, treatment of LR23 significantly increased solubility, and reduced the AGE-linked fluorescence of collagen of diabetic rats (P<0.05, FIGS. 2B, 3B and 4B). 5-ASA, which was found effective at low concentrations in the AGE-ELISA test, only showed cleavage effects in the papain test at these concentrations (FIG. 5).

Nonetheless, the limited number of collagen samples (2–3 samples) used in these studies may have contributed to statistical non-significance of the results of the other compounds rather than to their actual performance.

The AGE-breaking effects of these compounds were further evaluated on IgG-AGE crosslinked to the surface of RBCs. When compared to diabetic controls, RBCs treated with the

TABLE 2

Summarized Data on the Effects of
AGE-breaker Compounds on AGE Crosslinks that Form In Vivo

| Compound | Acid Solubility Test (% increase in solubility) | Papain digestion Assay (% decrease in fluorescence) | Pepsin Digestion Assay (% decrease in fluorescence) |
| --- | --- | --- | --- |
| LR20 | | | |
| 0.1 mM | 1.5 | 18.3 | 7.1 |
| 1.0 mM | 7.3 | 18.4 | 8.9 |
| 10 mM | 24.0 | 24.3 | 27.8 |
| LR23 | | | |
| 0.1 mM | 18.3 | 16.7 | 7.3 |
| 1.0 mM | 19.4 | 25.9 | 15.5 |
| 10 mM | 32.7 | 47.2 | 18.7 |
| LR99 | | | |
| 0.1 mM | 1.6 | 23.5 | 9.8 |
| 1.0 mM | 7.3 | 35.9 | 16.1 |
| 10 mM | 16.0 | 63.6 | 12.6 |
| LR102 | | | |
| 0.1 mM | 11.3 | 21.2 | 12.9 |
| 1.0 mM | 18.1 | 22.8 | 23.8 |
| 10 mM | 24.2 | 52.2 | 37.3 |
| 5-ASA | | | |
| 0.1 mM | 0 | 1.0 | 4.7 |
| 1.0 mM | 5.7 | 17.3 | 12.1 |
| 10 mM | 12.1 | 17.3 | 21.1 |
| Metformin | | | |
| 0.1 mM | 0 | 3.5 | 3.1 |
| 1.0 mM | 9.4 | 16.4 | 7.5 |
| 10 mM | 10.3 | 19.2 | 12.7 |

Figure 6:
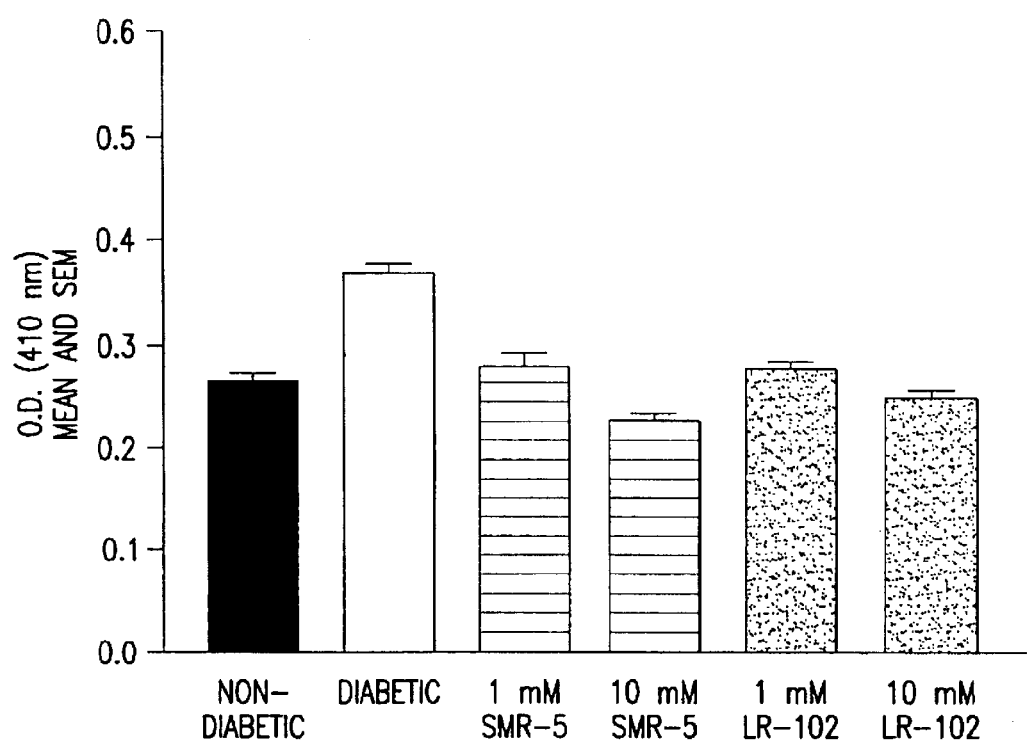
FIG. 6 shows the results of treating crosslinked IgG-AGE on rat RBCs with novel AGE-breakers (5-ASA (SMR-5) and LR102). Values are means ±SEM of three separate determinations.

All Values Are From Collagen Treated with the Compounds Relative to Untreated Collagen of Diabetic Rats. compounds had less IgG-AGE bound to their surface (FIG. 6). 5-ASA and LR102 treatments resulted in almost the same IgG-AGE content as that of non-diabetic control (P<0.05).

We also tested whether our compounds are capable of disaggregating both fibrillar native and glycated β-amyloid (AGE-βA) using the ThT binding assay and electron microscopy. Results of the ThT assay clearly confirmed the efficacy of the LR90, LR102 and 5-ASA on disaggregation of fibrillar forms of both native and glycated β-amyloid. Similarly, electron microscopic examination of the preparations of β-amyloid fibrils treated and untreated compounds revealed marked differences in the fibrillar form of the β-amyloid aggregates before and after treatment with the AGE-breakers. In control (untreated) preparations, β-amyloid shows dense fibrillar aggregate. In contrast, fibrils are less dense and non-uniform on the β-amyloid treated with an AGE-breaker. These results suggest that our novel AGE-breaker compounds have the ability of disaggregating the β-amyloid fibrillar structure.

Using the AGE-BSA-Collagen ELISA method, we found that many of our inhibitor compounds can also cleave and break AGE crosslinks. Many of them exhibited dose-dependent AGE-breaking activities, and a few like 5-ASA and metformin, are highly effective at low concentrations. Interestingly, we found 5-ASA to break AGE-BSA crosslinks even at 20 μM. This characteristic of 5-ASA may be one of the reasons this drug is effective in the treatment of "ulceritis colitis" and Crohn disease. Furthermore, 5-ASA may have some effects on reducing damage of β-amyloid content of Alzheimer plaques. Data on β-amyloid tests (performed at the Picower Institute for Medical Research in New York) revealed that this compound can disaggregate fibrillar forms of both native and glycated β-amyloid. Finally, this drug may have beneficial effects in reversing AGE crosslinks in rheumatoid arthritis, where accumulation of AGE in the collagen and an immunological response to IgG damaged by glyoxidation (AGE-IgG) has been reported recently (Lucey et al., 2000). Results of the IgG-AGE test indicated that 5-ASA treatment can significantly reduce IgG-AGE on the surface of RBCs.

The AGE breakers developed in our laboratory were effective in cleaving AGE crosslinks in the tail of diabetic rats as demonstrated by acid solubility and fluorescence measurements after pepsin and papain digestion. Furthermore several of the compounds were capable of breaking IgG-AGE crosslinks on the surface of red blood cells, as well as disaggregating both fibrillar forms of both native and glycated β-amyloid. Among the LR series of compounds, we found LR-23 and LR-102 as the most effective AGE-breakers. Metformin, a highly popular drug in the treatment of Type 2 diabetes, which we previously reported to inhibit AGE formation, also showed moderate AGE-breaking properties. Thus, it is conceivable based on our results that compounds with different functional groups can cleave and break AGE crosslinks.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Al-Abed, Y., Liebich, H., Voelter, W., and Bucala, R. Hydroxyalkenal formation induced by advanced glycosylation of low density lipoprotein. J. Biol. Chem 271:2892–2896, 1996.

Al-Abed, Y., Kapurniotu, A., Bucala, R., Advanced glycation end products: Detection and reversal. Methods in Enzymology, 309:152–172, 1999.

Asif, M., Egan, J., Vasan, S., Jyothirmayi, G. N., Masurekar, M. R., Lopez, S., Williams, C., Torres, R. L., Wagle, D., Ulrich, P., Cerami, A., Brines, M., and Regan, T. J. An advanced glycation endproduct cross-link breaker can reverse age-related increases in myocardial stiffness. Proc. Natl. Acad. Sci., USA 97:2809–2813, 2000.

Bailey, A. J., Paul, R. G., and Knott, L. Mechanisms of maturation and ageing of collagen. Mechanisms of Ageing and Development, 106:1–56, 1998.

Baynes, J. W., and Thorpe, S. R. Perspective in diabetes: role of oxidative stress in diabetic complications: A new perspective on an old paradigm. Diabetes 48:1–9, 1999.

Beisswenger, P., Smith, K., Howell, S., Touchette, A., and Szwergold, B. Accelerated diabetic nephropathy is associated with increased methylglyoxal production. Am. Diab. Assoc., 58th Annual Meeting, #312, Chicago, June 1998.

Boel, E., Selmer, J., Flodgaard, H. J., Jensen, T., Diabetic late complications: will aldose reductase inhibitors or inhibitors of advanced glycosylation endproduct formation hold promise? *J. Diab. Compl.* 9:104–129, 1995.

Brownlee, M. Lilly Lecture 1993. Glycation and diabetic complications. *Diabetes,* 43:836–841, 1994.

Bucala, R. Lipid and lipoprotein modification by advanced glycosylation end-products: Role in atherosclerosis. *Experimental Physiology,* 82:327–337, 1997.

Bucala, R. and Cerami, A. Advanced glycosylation: chemistry, biology and implications for diabetes and aging. *Adv. Pharmacol* 23:1–34, 1992.

Bucala, R. and Rahbar, S. Protein glycation and vascular disease in Endocrinology of cardiovascular function. Edited by E. R. Levin and J. L. Nadler, Kluwer Acad. Publishers, p 159–180, 1998.

Bucala, R., Model, P., Cerami, A. Modification of DNA by reducing sugars: a possible mechanism for nucleic acid aging and age-related dysfunction in gene expression. *Proc. Natl. Acad Sci. U.S.A.,* 81:105–109, 1984.

Bucala,, R., Makita, Z., Koschinsky, T., Cerami, A., Vlassara, H. Lipid advanced glycosylation: pathway for lipid oxidation in vivo. *Proc. Natl. Acad. Sci. USA* 90:6434–6438, 1993.

Bucala, R., Makita, Z., Vega, G., Grundy, S., Koschinsky, T., Cerami, A. and Vlassara, H. Modification of low density lipoprotein by advanced glycation end products contributes to dyslipidemia of diabetes and renal insufficiency. *Proc. Natl. Acad. Sci. U.S.A.,* 91:9441–9445, 1994.

Cooper, M. E., Thallas, V., Forbes, J., Scalbert, E., Sastra, S., Darby, I., and Soulis, T. The cross-link breaker, N-phenacylthiazolium bromide prevents vascular advanced glycation end-product accumulation. *Diabetologia,* 43:660–664, 2000.

Creemers, L. B., Jansen, D.C., van Veen-Reurings, A., van den Bos, T., and Everts, V. Microassay for the assessment of low levels of hydroxyproline. *BioTechniques,* 22:656–658, 1997.

The Diabetes Control and Complications Trial Research Group: The effect of intensive treatment of diabetes on the development and progression of long-term complications in insulin-dependent diabetesmellitus. *N Engl J Med* 329:977–986,1993.

Forbes, J. M., Soulis, T., Thallus, V., et al. Renoprotective effects of a novel inhibitor of advanced glycation. *Diabetologia,* 44:108–114 (2001).

Gilcrease, M. Z., and Hoover, R. L. Human monocyte interactions with non-enzymatically glycated collagen. *Diabetologia,* 35:160–164, 1992.

He, C., Sabol, J., Mitsuhashi, T., and Vlassara, H. Dietary glycotoxins: Inhibition of reactive products by aminoguanidine facilitates renal clearance and reduces tissue sequestration. *Diabetes,* 48:1308–1315, 1999.

Hedrick C C, Thorpe S R, Fu M X, Harper C M, Yoo J, Kim S M, Wong H, Peters A L. Glycation impairs high-density lipoprotein function. *Diabetologia* 43:312–320, 2000.

Horie, K., Miyata, T., Maeda, K., Miyata, S. Sugiyama, S., Sakai, H., Strihou, C., Monnier, V. M., Witztum, J. L., and Kurokawa, K. Immunohistochemical colocalization of glycoxidation products and lipid peroxidation products in diabetic renal glomerular lesions. Implication for glycoxidative stress in the pathogenesis of diabetic nephropathy. *J. Clin. Invest.* 100:2995–3004, 1997.

Iijima, K., Murata, M., Takahara, H., Irie, S., and Fujimoto, D. Identification of $N^\omega$-carboxymethylarginine as a novel acid-labile advanced glycation end product in collagen. *Biochem. J.,* 347Pt1:23–27, 2000

Kapurniotu, A., Bernhagen, J., Greenfield, N., Al-Abed, Y., Teichberg, S., Frank, R. W., Voelter, W., and Bucala, R. Contribution of advanced glycosylation to the amyloidogenicity of islet amyloid polypeptide. *Eur. J. Biochem.,* 251:208–216, 1998.

Khalifah, R. G., Baynes, J. W., and Hudson, B. G. Amadorins: Novel post-amadori inhibitors of advanced glycation reactions. *Biochem. Biophys. Res. Commun.* 257:251–258, 1999.

Klunk, W. E., Jacob, R. F., and Mason, R. P. Quantifying amyloid β-peptide (Aβ) aggregation using the Congo Red-Aβ (CR-Aβ) spectrophotometric assay. *Analytical Biochemistry,* 266:66–76, 1999.

Kochakian, M., Manjula, B. N., and Egan, J. J. Chronic dosing with aminoguanidine and novel advanced glycosylation end product-formation inhibitors ameliorates cross-linking of tail tendon collagen in STZ-induced diabetic rats. *Diabetes* 45:1694–1700, 1996.

Koschinsky, T., He, C. J., Mitsuhashi, T., Bucala, R., Liu, C. Buenting, C., Heitmann, K. and Vlassara, H. Orally absorbed reactive glycation products (glycotoxins): An environmental risk factor in diabetic nephropathy. *Proc Natl. Acad. Sci. U.S.A.* 94:6474–6479, 1997.

Lapolla, A., Fedele, D., Garbeglio, M., Martano, L., Tonani, R., Seraglia, R., Favretto, D., Fedrigo, M. A., and Traldi, P. Matrix-assisted laser desorption/ionization mass spectrometry, enzymatic digestion, and molecular modeling in the study of nonenzymatic glycation of IgG. *J. Am. Soc. Mass. Spectrom,* 11:153–159, 2000.

Loske, C., Gercemann, A., Schepl, W., et al. Transition metal-mediated glycoxidation accelerates cross-linking of β-amyloid peptide. *Eur. J. Biochem.,* 267:4171–4178, 2000.

Lucey, M. D., Newkirk, M. M., Neville, C., Lepage, K., and Fortin, P. R. Association between IgM response to IgG damaged by glyoxidation and disease activity in rheumatoid arthritis. *J. Rheumatol.* 27:319–323, 2000.

Makita, Z., Radoff, S., Rayfield, E. J., Yang, Z. H., Skolnik, E., Delaney, V., Friedman, E. A., Cerami, A. and Vlassara, H. N. Advanced glycosylation end products in patients with diabetic nephropathy. *N. Eng. J. Med.* 325:836–842, 1991.

Makita, Z., Bucala, R., Rayfield, E. J., Friedman, E. A., Kaufman, A. M., Korbet, S. M., Barth, R. H., Winston, J. A., Fuh, H., Manogue, K. R., Cerami, A. and Vlassara, H. Reactive glycosylation endproducts in diabetic uraemia and treatment of renal failure. *Lancet,* 343:1519–1522, 1994.

Matsumoto, K., Ikeda, K., Horiuchi, S., Zhao, H., and Abraham, E. C. Immunochemical evidence for increased formation of advanced glycation end products and inhibition by aminoguanidine in diabetic rat lenses. *Biochem. Biophys. Res. Commun.,* 241, 352–354, 1997.

McLellan, A. C., Thornalley, P. J., Benn, J. and Sonksen, P. H. Glyoxalase system in clinical diabetes mellitus and correlation with diabetic complications. *Clin. Sci. (Colch),* 87:21–29, 1994.

Munch, G., Mayer, S., Michaelis, J., Hipkiss, A. R., et al. Influence of advanced glycation end-products and AGE-inhibitors on nucleation-dependent polymerization of β-amyloid peptide. *Biochim. Biophys. Acta,* 1360:17–29 (1997).

Onorato, J. M., Thorpe, S. R., and Baynes, J. W. Immunohistochemical and ELISA assays for biomarkers of oxidative stress in aging and disease. *Ann, N.Y. Acad. Sci.* 854:277–290, 1998.

Oturai, P. S., Christensen, M., Rolin, B., et al. Effects of advanced glycation end-product inhibition and cross-link breakage in diabetic rats. *Metabolism,* 49:996–1000, 2000.

Park, L., Raman, K. G., Lee, K. J., Lu, Y., Ferran, L. J., Chow, W. S., Stern, D., and Schmidt, A. M., Suppression of accelerated diabetic atherosclerosis by the soluble receptor for advanced glycation endproducts. *Nature Med.* 4:1025–1031, 1998

Phillips, S. A., and Thornalley, P. J. The formation of methylglyoxal from triose phosphates. Investigation using a specific assay for methylglyoxal. *Eur. J. Biochem.* 212:101–105, 1993.

Rahbar, S., Kumar Yernini, K., Scott, S., Gonzales, N., and Lalezari, I. Novel inhibitors of advanced glycation endproducts. *Biochem. Biophys. Res. Commun.*, 262:651–656, 1999.

Rahbar, S., Yerneni, K., Scott, S., Gonzales, N., and Lalezari, I. Novel inhibitors of advanced glycation endproducts (PART II), *Mol. Cell. Biol. Res. Commun.*, 3:360–366 (2000a).

Rahbar, S., Natarajan, R., Yerneni, K., Scott, S., Gonzales, N. and Nadler, J. L., Evidence that pioglitazone, metformin and pentoxifylline are inhibitors of glycation. *Clin. Chim. Acta*, 301:65–77, 2000b.

Requena, J. R., Ahmed, M. U., Fountain, C. W., Degenhardt, T. P., Reddy, S. R., Perez, C., Lyons, T. J., Jenkins, A. J., Baynes, J. W., Thorpe, S. R. Carboxymethylethanolamine, a biomarker of phospholipid modification during the Maillard reaction IN VIVO. *J. Biol. Chem.* 272:17473–17479, 1997.

Sajithlal, G. B., Chithra, P., and Chandrakasan, G. Effect of curcumin on the advanced glycation and cross-linking of collagen in diabetic rats. *Biochem. Pharmacol.*, 56:1607–1614, 1998.

Schalkwijk, C. G., Vermeer, M. A., Stehouwer, C. D. A., te Koppele J., Princen, H. M. G., Van Hinsbergh, V. W. M. Effect of methylglyoxal on the physico-chemical and biological properties of low-density lipoprotein. *Biochim. Biophys. Acta* 1394:187–198, 1998.

Schmidt, A. M., Hasu, M., Popov, D., Zhang, J. H., Chen, J., Yan, S. D., Brett, J., Cao, R., Kuwabara, K., Costache, J., Simionescu, N. and Stern, D. Receptor for advanced glycation end products (AGEs) has a central role in vessel wall interactions and gene activation in response to circulating AGE protein. *Proc. Natl. Acad. Sci, USA*, 91:8807–8811, 1994.

Silbiger, S., Crowley, S., Shan, Z., Brownlee, M., Satriano, J., Schlondorff, D. Nonenzymatic glycation of mesangial matrix and prolonged exposure of mesangial matrix to elevated glucose reduces collagen synthesis and proteoglycan charge. *Kidney Int.* 43:853–864, 1993.

Slatter, D. A., Bolton, C. H., and Bailey, A. J. The importance of lipid-derived malondialdehyde in diabetes mellitus. *Diabetologia*, 43:550–557, 2000.

Soulis-Liparota, T., Cooper, M., Papazoglou, D., Clarke, B. and Jerums, G. Retardation by aminoguanidine of development of albuminuria, mesangial expansion, and tissue fluorescence in streptozocin-induced diabetic rat. *Diabetes*, 40:1328–1334, 1991.

Soulis, T., Sastra, S., Thallas, V., et al. A novel inhibitor of advanced glycation end-product formation inhibits mesenteric vascular hypertrophy in experimental diabetes. *Diabetologia*, 42:472–479, 1999.

Stefek, M., Gajdosik, A., Gajdosikova, A., and Krizanova, L. p-Dimethylaminobenzaldehyde-reactive substances in tail tendon collagen of streptozotocin-diabetic rats: temporal relation to biomechanical properties and advanced glycation endproduct (AGE)-related fluorescence. *Biochim. Biophys. Acta*, 1502:398–404, 2000.

Takahashi, M., Pischetsrieder, M., Monnier, V. M. Isolation, purification, and characterization of amadoriase isoenzymes (fructosyl amine-oxygen oxidoreductase EC 1.5.3) from Aspergillus sp. *J Biol Chem,* 272:3437–3443, 1997

Thornalley, P. J., and Minhas, H. S. Rapid hydrolysis and slow alpha,beta-dicarbonyl cleavage of an agent proposed to cleave glucose-derived protein cross-links. *Biochem. Pharmacol.* 57:303–307, 1999.

Tjernberg, L. O., Callaway, D. J. E., Tjernberg, A., Hahne, S., Lilliehöök, C., Terenius, L., Thyberg, J., and Nordstedt, C. A molecular model of Alzheimer amyloid β-peptide fibril formation. *J. Biol. Chem.,* 274:12619–12625, 1999.

Ulrich, P., and Zhang, X. Pharmacological reversal of advanced glycation end-product-mediated protein crosslinking. *Diabetologia,* 40: S157–S159, 1997.

Vaitkevicius, P. V., Lane, M., Spurgeon, H. et al. A cross-link breaker has sustained effects on arterial and ventricular properties in older rhesus monkey. *Proc. Natl. Acad. Sci. USA.,* 98:1171–1175, 2001.

Vasan, S., Zhang, X., Zhang, X. I., Kapurniotu, A., Bernhagen, J., Teichberg, S., Basgen, J., Wagle, D., Shih, D., Terlecky, I., Bucala, R., Cerami, A., Egan, J., and Ulrich, P. An agent cleaving glucose-derived protein crosslinks in vitro and in vivo. *Nature,* 382:275–278, 1996.

Verzijl, N., DeGroot, J., Oldehinkel, E., et al. Age-related acumulation of Maillard reaction products in human articular cartilage collagen. *Biochem. J.,* 350:381–387, 2000.

Vlassara, H., Fuh, H., Donnelly, T., and Cybulsky, M. Advanced glycation endproducts promote adhesion molecule (VCAM-1, ICAM-1) expression and atheroma formation in normal rabbits. *Mol Medicine* 1:447–456, 1995.

Westwood, M. E., Argirov, O. K., Abordo, E. A., and Thornalley, P. J. Methylglyoxal-modified arginine residues—a signal for receptor-mediated endocytosis and degradation of proteins by monocytic THP-1 cells. *Biochim. Biophys. Acta* 1356:84–94, 1997.

Wolffenbuttel, B. H. R., Boulanger, C. M., Crijns, F. R. L., Huijberts, M. S. P., Poitevin, P., Swennen, G. N. M., Vasan, S., Egan, J. J., Ulrich, P., Cerami, A., and Levy, B. I. Breakers of advanced glycation end products restore large artery properties in experimental diabetes. *Proc. Natl. Acad. Sci., USA,* 95:4630–4634, 1998.

Yan, H. and Harding, J. J. Inactivation and loss of antigenicity of esterase by sugars and a steroid. *Biochim. Biophys. Acta,* 1454:183–190, 1999.

Yan, S. D., Stern, D., and Schmidt, A. M. What's the RAGE? The receptor for advanced glycation end products (RAGE) and the dark side of glucose. *Eur. J. Clin. Invest.,* 27:179–181, 1997.

Yang, S., Thorpe, S. R., and Baynes, J. W. AGE-breakers fail to break cross-links in skin collagen of diabetic rats. *Diabetes,* 49 (Suppl. 1), A130, 2000.

Yim, H. S., Kang, S. O., Hah, Y. C., Chock, P. B., and Yim, M. B. Free radicals generated during the glycation reaction of amino acids by methylglyoxal. A model study of protein-cross-linked free radicals. *J. Biol. Chem.* 270:28228–28233, 1995.

What is claimed is:

1. A method for cleaving glycation endproducts or cross-linked proteins in an organism, wherein said method comprises administering an effective amount of a compound or a pharmaceutically acceptable salt of said compound to said organism wherein said compound is selected from the group consisting of:

LR-102: 1,4-benzene-bis[4-methyleneaminophenoxyisobutyric acid]; and

LR-99: 4-[3,5-dichlorophenylureidophenoxyisobutyryl]-4-aminobenzoic acid.

2. The method of claim 1 wherein said compound is 1,4-benzene-bis [4-methyleneaminophenoxyisobutyric acid].

3. The method of claim 1 wherein said compound is 4-[3,5-dichlorophenylureidophenoxyisobutyryl]-4-aminobenzoic acid.

4. A method of treating deleterious effects of aging in an organism, wherein said effects are formation of glycation endproducts or protein cross-linking, wherein said method comprises administering an effective amount of a compound or a pharmaceutically acceptable salt of said compound to said organism wherein said compound is selected from the group consisting of:

LR-102: 1,4-benzene-bis[4-methyleneaminophenoxyisobutyric acid]; and

LR-99: 4-[(3,5-dichlorophenylureidophenoxyisobutyryl]-4-aminobenzoic acid.

5. The method of claim 4 wherein said compound is 1,4-benzene-bis[4-methyleneaminophenoxyisobutyric acid].

6. The method of claim 4 wherein said compound is 4-[3,5-dichlorophenylureidophenoxyisobutyryl]-4-aminobenzoic acid.

7. A method of treating complications resulting from diabetes, wherein said complications result from formation of glycation endproducts or protein cross-linking, wherein said method comprises administering an effective amount of a compound or a pharmaceutically acceptable salt of said compound to said organism wherein said compound is selected from the group consisting of:

LR-102: 1,4-benzene-bis[4-methyleneaminophenoxyisobutyric acid]; and

LR-99: 4-[(3,5-dichlorophenylureidophenoxyisobutyryl]-4-aminobenzoic acid.

8. The method of claim 7 wherein said compound is 1,4-benzene-bis-[4-methyleneaminophenoxyisobutyric acid].

9. The method of claim 7 wherein said compound is 4-[3,5-dichlorophenylureidophenoxyisobutyryl]-4-aminobenzoic acid.

10. A method of treating a patient having rheumatoid arthritis, Alzbeimer's disease, uremia, neurotoxicity, or atherosclerosis by cleaving advanced glycation endproducts or cross-linked proteins, wherein said method comprises administering an effective amount of a compound or a pharmaceutically acceptable salt of said compound to said patient wherein said compound is selected from the group consisting of:

LR-102: 1,4-benzene-bis[4-methyleneaminophenoxyisobutyric acid]; and

LR-99: 4-[(3,5-dichlorophenylureidophenoxyisobutyryl]-4-aminobenzoic acid.

11. The method of claim 10 wherein said compound is 1,4-benzene-bis 4[methyleneaminophenoxyisobutyric acid].

12. The method of claim 10 wherein said compound is 4-[(3,5-dichlorphenylureidophenoxyisobutyryl]-4-aminobenzoic acid.

* * * * *